(12) United States Patent
Neumayr et al.

(10) Patent No.: US 6,720,057 B1
(45) Date of Patent: Apr. 13, 2004

(54) METHOD FOR PRODUCING A CELLULOSE FIBRE FROM HYDROCELLULOSE

(76) Inventors: Achim Neumayr, Demhartstrasse 8, Villenbach (DE), D-89444; Herbert Hasl, Puerschlingweg 4, Oberammergau (DE), D-82487

( * ) Notice: Subject to any disclaimer, the term of this patent is extended or adjusted under 35 U.S.C. 154(b) by 0 days.

(21) Appl. No.: 09/485,277
(22) PCT Filed: Aug. 7, 1998
(86) PCT No.: PCT/EP98/05030
§ 371 (c)(1), (2), (4) Date: May 17, 2000
(87) PCT Pub. No.: WO99/07926
PCT Pub. Date: Feb. 18, 1999

(30) Foreign Application Priority Data

Aug. 7, 1997 (DE) .......................... 197 34 239
Mar. 6, 1998 (DE) .......................... 198 09 765

(51) Int. Cl.[7] .............................. D01F 2/06; D01F 2/08; D01F 11/02; B32B 3/02
(52) U.S. Cl. ........................... 428/92; 428/97; 264/186; 264/187; 264/188; 264/195; 264/196
(58) Field of Search ........................ 428/92, 97, 95, 428/397, 400; 264/188, 195, 196, 186, 187

(56) References Cited

U.S. PATENT DOCUMENTS

| | | | | |
|---|---|---|---|---|
| 2,046,670 A | | 7/1936 | Beattey | |
| 4,136,255 A | * | 1/1979 | Franks | 536/57 |
| 4,210,747 A | * | 7/1980 | Sorsa et al. | 162/72 |
| 4,242,405 A | * | 12/1980 | Bockno | 264/188 |
| 4,364,890 A | * | 12/1982 | Treiber et al. | 106/166.5 |
| 5,275,699 A | * | 1/1994 | Allan et al. | 162/181.2 |
| 5,458,963 A | * | 10/1995 | Meirowitz et al. | 428/221 |
| 5,482,776 A | * | 1/1996 | Nishiyama et al. | 428/364 |

FOREIGN PATENT DOCUMENTS

| | | | | |
|---|---|---|---|---|
| DE | 27 20 087 A1 | 11/1977 | | |
| DE | 298 01 027 U1 | 5/1998 | | |
| EP | 0 574 762 A1 | 5/1993 | | |
| EP | 580879 B1 | * 4/1996 | | A61M/1/18 |
| GB | 369912 | 3/1932 | | |
| GB | 757233 | 9/1956 | | |
| GB | 761511 | 11/1956 | | |
| GB | 2062652 A | * 5/1981 | | C08L/1/00 |
| JP | 2277846 A | 11/1990 | | |

OTHER PUBLICATIONS

M.L. Joseph, Introductory Textile Science, 5th ed., CBS College Publishing, 1986, pp. 82–87.*

* cited by examiner

Primary Examiner—Cheryl A. Juska
(74) Attorney, Agent, or Firm—Jenkins, Wilson & Taylor, P.A.

(57) ABSTRACT

The invention described here concerns a process to permit the manufacture of a cellulose fibre from hydrate cellulose with an extremely large surface area which may be used for the preparation of a fabric characterized by a high absorptive power, good liquid-retention properties, high grease-solvent properties as well as particle-absorbing properties, which is suitable for making products that are themselves easy to clean, which can be used for cleaning and decontamination as well as to reduce the surface tension of water and which can be disposed of without damage to the environment.

58 Claims, 15 Drawing Sheets

Scanning electron micrographs of the samples

Scanning electron micrographs of microtome sections (approx. 3 μm thick)

x, y: spacing between fabric cloths

Tensiometer to measure the surface tension

Surface tension-reducing effect of the fabric L01 as a function of rinsing the fabric Surface tension-reducing effect of the fabric L02 as a function of rinsing the fabric Surface tension-reducing effect of the fabric S10 as a function of rinsing the fabric Surface tension-reducing effect of the double-sided fabric L01

Surface tension-reducing effect of the double-sided fabric L02

Surface tension-reducing effect of the double-sided fabric S10

Surface tension with fabrics which remain in the water

Surface tension-reducing effect of the fabric L01 before and after the drying phase (mean values)

Test set-up to determine the water-absorbing capacity

METHOD FOR PRODUCING A CELLULOSE FIBRE FROM HYDROCELLULOSE

TECHNICAL FIELD

The invention described here concerns a process to manufacture a cellulose fibre from hydrate cellulose, a cellulose fibre obtainable by this process, as well as a fabric which contains these cellulose fibres and the use of this fabric.

BACKGROUND ART

Absorbent fibrous materials which can also be applied for cleaning purposes are already known. Examples are cross-linked carboxy methyl cellulose (CMC), which can be manufactured in accordance with the process described in CH-A-491140, or viscose fibres, which contain hydrophilic polymer substances such as polyacrylic acid (BE-A-2324589), poly-N-vinyl pyrrolidone or CMC (DE-A-25 50 345), alginic acid (DE-A-27 50 622) or other copolymers (DE-A-27 50 900). Besides their high absorptive power, these fibres have good water-retention properties. The manufacture of these fibres, however, is associated with a high degree of technical complexity, and some of these fibres contain substances which either do not biodegrade at all or only with difficulty, so that natural disposal (e.g. composting) of the fibres subsequent to their use not possible.

DISCLOSURE OF THE INVENTION

The object of this invention is to provide a process to permit the manufacture of a cellulose fibre from hydrate cellulose with an extremely large surface area and which biodegrades easily. Another object of the invention is to provide a fabric made from these fibres which is characterised by a high absorptive power, good water-retention properties, high grease-solvent properties as well as particle-absorbing properties, which is suitable for making products that are themselves easy to clean, which can be used for cleaning and decontamination as well as to reduce the surface tension of water and which can be disposed of without damage to the environment.

The above-described objects are solved by the invention-design process to manufacture a cellulose fibre from hydrate cellulose which comprises the following steps:

a) Treatment of wood pulp derived from shoots no older than 1 year of deciduous trees or conifers with an alkali metal hydroxide solution in order to obtain an alkali cellulose;

b) pressing out of the superfluous alkali metal hydroxide solution from the obtained alkali cellulose;

c) shredding of the alkali cellulose into crumbs;

d) ripening of the alkali cellulose crumbs to a maturity of between 5° and 30° Hottenroth;

e) application of the wet sulphide process to treat the ripened crumbs in order to sulphidise the cellulose;

f) rinsing and diluting of the sulphidised cellulose with water in order to obtain a spinning solution;

g) subsequent ripening of the rinsed and diluted cellulose to a maturity of between 5° and 30° Hottenroth;

h) filtering and downstream deaeration of the spinning solution;

i) injection of the spinning solution into a regenerating bath under application of spinnerets;

j) stripping off the coagulating fibres with simultaneous twisting in order to obtain twisted fibres;

k) dehydrating of the twisted fibres;

l) desulphurisation of the twisted fibres;

m) washing of the twisted fibres with water;

n) predehydrating of the twisted fibres; and o) drying of the twisted fibres;

and by a fabric comprising a backing fabric and a pile woven into the backing fabric containing these fibres.

DETAILED DESCRIPTION OF THE INVENTION

Figures 1, 2, 3, 4, 5, 6:
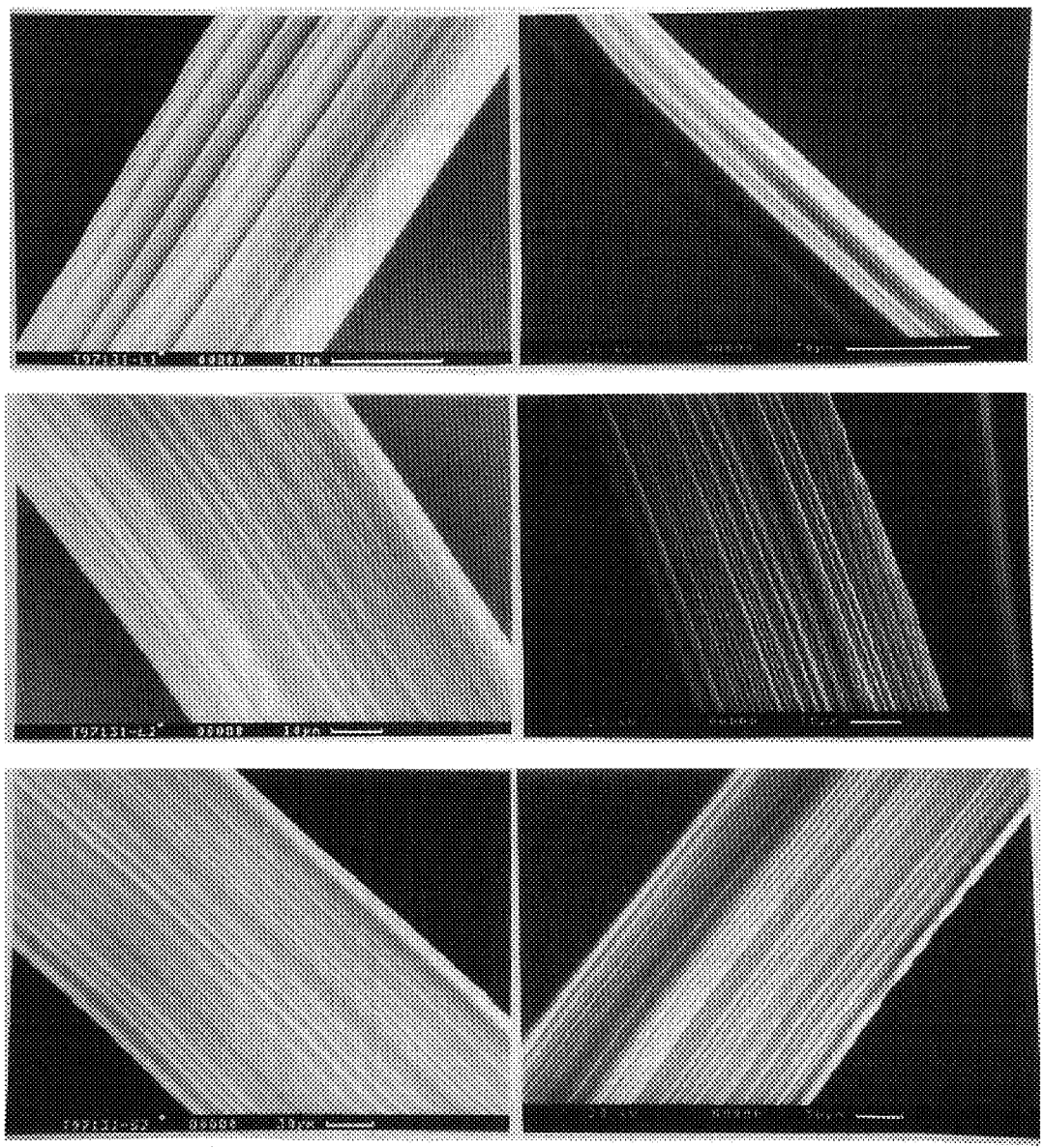
FIGS. 1 to 6 show the microstructure of the invention-design fibres.
Figures 7, 8, 9, 10, 11, 12:
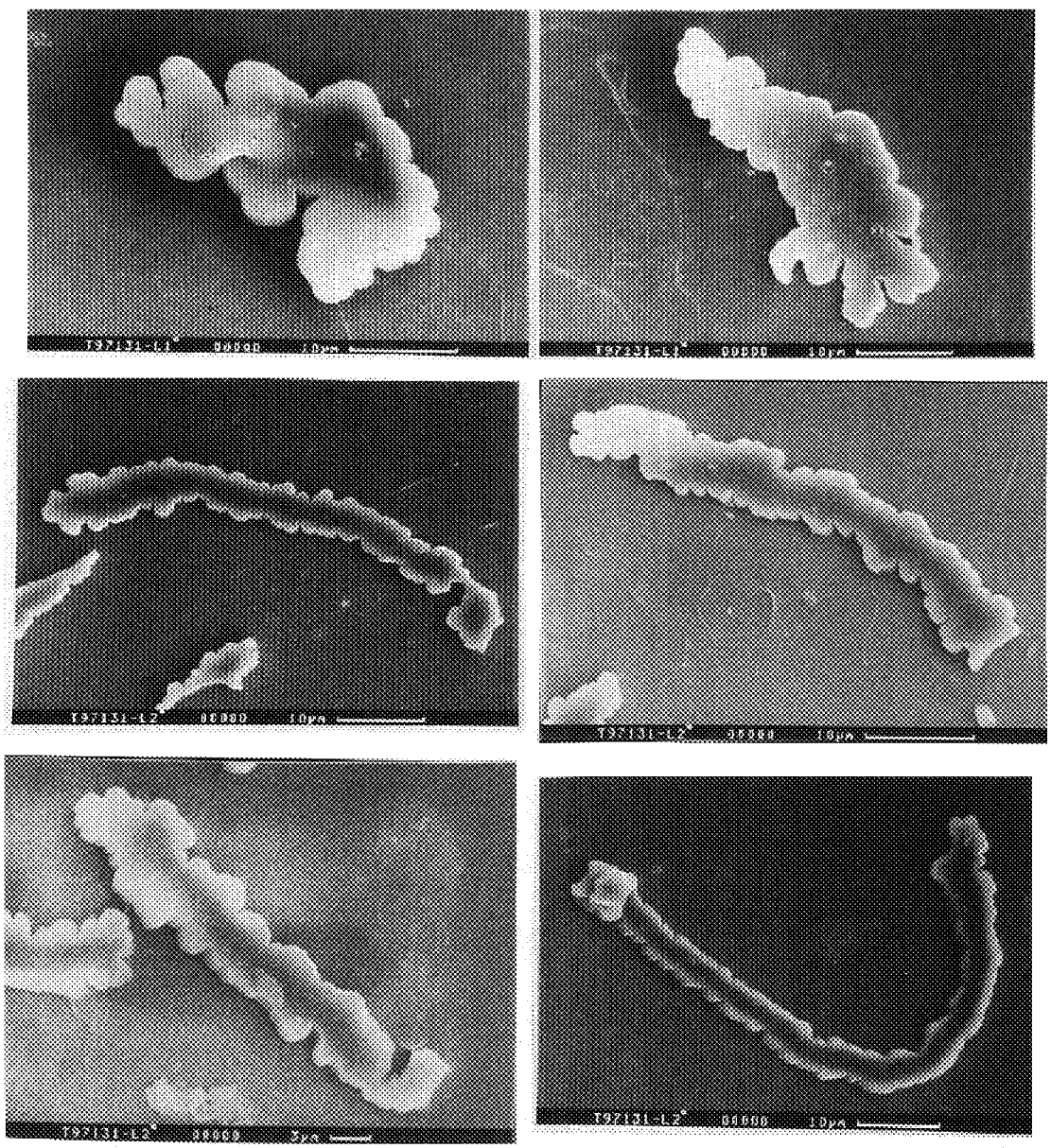
FIGS. 7 to 15 show the macrostructure of the invention-design fibres.
Figures 13, 14, 15:
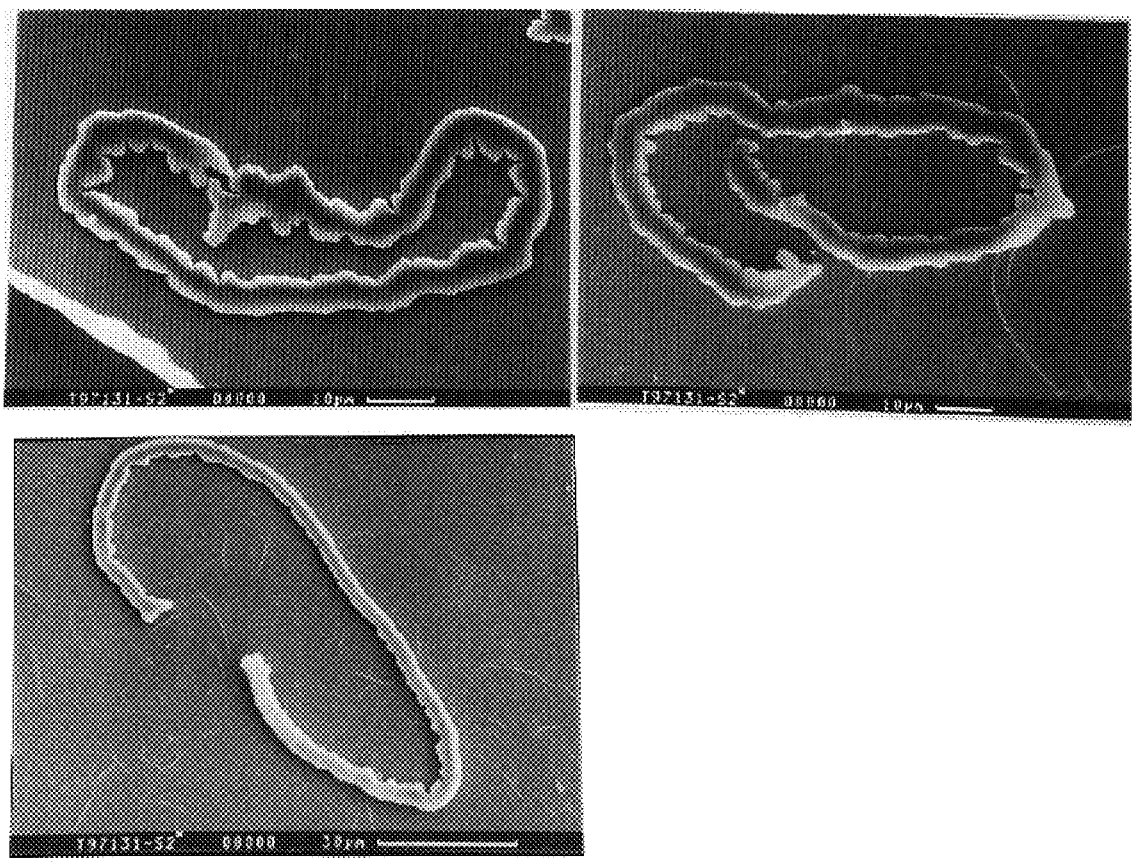

The invention-design process permits the manufacture of a biodegradable cellulose fibre from hydrate cellulose $(C_6H_{10}O_5)_n$, whose microstructure displays fibre-parallel lamellae. The preferred lamella spacing lies in the range between 1 nm and 5 µm, whereas the range between 200 nm and 1 µm is ideal. Another particularly good range is between 1 and 20 nm. As a result of this microstructure, the fibre has an extremely large surface area. In a preferred design, the invention-design fibre is birefractive. The microstructure and the macrostructure of the invention-design fibres were determined by means of the processes described below.

The microstructure of various invention-design fibres which were designated L1, L2, and S2 in the tests is shown in FIGS. 1 to 6. The purpose of the tests was to analyse the fibres as complete fibres with respect to the surface structure using a scanning electron microscope. The macrostructure of the fibres, shown in FIGS. 7 to 15, was analysed as a microtome section. The microtome sections were prepared by embedding the fibres in PMMA, cutting them and then extracting them from the embedding medium. The exposure of the fibres to high temperatures was thereby kept as low as possible.

FIGS. 1 to 6 show the resultant microstructures viewed from above. All invention-design fibres have a fibre-parallel lamellar structure. However, these figures are not able to give any indication of the cross-sectional structure (macrostructure). It is the microtome sections which show the cross-sectional structures, as shown in FIGS. 7 to 15. Fibre L1 was prepared using an oval spinneret, whereas an extended slit-shaped spinneret was used to prepare fibres L2 and S2. The qualitative results of the tests are summarised in the following table (Table 1).

TABLE 1

|  | Fibre type | | |
| --- | --- | --- | --- |
|  | L1 | L2 | S2 |
| Cross-sectional form (macrostructure) | globular, strongly fissured | lamellar, fissured | lamellar, fissured |
| Spec. surface area (qualitative) | extremely large | medium | large |
| Position of surface structure (incisions) | on all sides | on all sides | mainly on one side, i.e. on the inside after curling |
| Max. fibre width [μm] | approx. 35 | approx. 80 | approx. 200 |
| Curling effect after cutting (indication of internal stress) | not detectable | low | high |

Wood pulp derived from shoots no older than 1 year of deciduous trees or conifers was used to prepare the invention-design fibre. It is particularly easy to remove the lignin from such a base material. Ideally, wood pulp derived from shoots no older than 1 year of false acacia trees, teak trees, bongassi trees or bamboo is used, although wood pulp derived from shoots no older than 1 year of comparable European trees can also be used. The lignin content of the less-than-one-year-old shoots used should be as low as possible and is preferably no more than 7%. In a particularly preferred invention design, the lignin content of the base material is no more than 5%, and ideal is no more than 2%.

This wood pulp is treated with an alkali metal hydroxide solution, preferably at a temperature of between 15 and 25° C., in order to obtain an alkali cellulose. It is preferable to use a sodium hydroxide solution which contains between 150 and 350 g/l of sodium hydroxide as the alkali metal hydroxide solution. A sodium hydroxide content of approx. 300 g/l is particularly favourable.

The superfluous alkali metal hydroxide solution is then pressed out of the resultant alkali cellulose, e.g. under application of a submersible press.

The alkali cellulose is then shredded into crumbs, whereby shredding can include a coarse comminution step (e.g. in a pre-shredder) and a fine comminution step (e.g. in a disc mill).

The crumbs are then fed, for example, to a maturing drum and ripened to a maturity of between 50° and 30° Hottenroth, preferred is a maturity of between 8° and 12° Hottenroth, and a maturity of approx. 10° Hottenroth is ideal. The preferred temperature during the ripening process is between 60 and 80° C., particularly favourable is a temperature of between 65 and 75° C., and approx. 72° C. is absolutely ideal. The ripening process can then be slowed down by reducing the temperature to between 40 and 50° C., or preferably to approx. 45° C.

The ripened crumbs are subsequently treated under application of the conventional wet sulphide process in order to sulphidise the cellulose. The wet sulphide process is preferably carried out in a solution containing carbon disulphide, sodium hydroxide and BEROL®, a surfactant. The preferred carbon disulphide content of the solution is between 150 and 250 g/l, particularly favourable is between 180 and 210 g/l, and the preferred content of sodium hydroxide is between 250 and 350 g/l, particularly favourable is between 280 and 320 g/l, and the preferred content of BEROL is between 100 and 200 g/l, particularly favourable is approx. 150 g/l. The most preferable type of BEROL® surfactant used for this process step is one of the commercially available products from Berol-Kemie Ltd., 44401 Stennungsund, Sweden.

After sulphidisation, the sulphidised cellulose is rinsed and then diluted with water to produce a spinning solution. The cellulose is then subsequently ripened to a maturity of between 5° and 30° Hottenroth, whereby a maturity of between 8° and 12° Hottenroth is preferred. The degree of ripeness achieved during initial ripening is diminished by the sulphidisation process and by rinsing and diluting the sulphidised cellulose, and it is not until a subsequent ripening process is carried out that the desired degree of ripeness is finally achieved. In practical operation, it is not always easy to control the degree of ripeness with great accuracy. In this case, two or more batches of spinning solutions can be mixed in order to achieve the desired degree of ripeness.

The downstream filtration of the spinning solution may be carried out under application of filter presses. The spinning solution is then deaerated.

The deaerated spinning solution is introduced by means of spinnerets into a regenerating bath, preferably at a temperature of between 35 and 45° C., and ideally at a temperature of approx. 40° C. A suitable regenerating bath contains between 70 and 160 g/l of sulphuric acid, preferred is between 90 and 140 g/l, and approx. 120 g/l is ideal, plus between 0.3 and 4 g/l of zinc sulphate, preferred is between 0.5 and 2 g/l, and approx. 1 g/l is ideal, plus between 0.05 and 1 g/l of BEROL®, a surfactant, preferred is between 0.1 and 0.7 g/l, and approx. 0.4 g/l is ideal. The most preferable type of BEROL® surfactant used for this process step is one of the commercially available products from Berol-Kemie Ltd., 44401 Stennungsund, Sweden. The spinnerets used can be oval to long-slit-shaped, and are heated to keep them within a preferred temperature range of 55–75° C., particularly favourable is between 65 and 70° C., and approx. 67° C. is absolutely ideal.

The fibres are stripped off as they coagulate and simultaneously twisted in order to obtain twisted fibres, which are then dehydrated. A sulphuric acid solution, for example, can be used for dehydrating, whereby a content of ≦15 g/l of sulphuric acid is preferred and ≦10 g/l is ideal.

Desulphurisation of the twisted fibres is generally carried out in a sodium sulphate solution, which preferably contains between 2 and 5 g/l of sodium sulphate and ideally approx. 3 g/l. Other desulphurisation processes are also possible. The fibres are then washed with water.

After washing, the fibres can be further treated, for example in order to modify the optical properties of the fibres. Titanium dioxide, for example, can be used to give the fibres a dull finish.

The fibres are then predehydrated and dried, whereby if the lamellar structure of the fibres is to remain intact, as little mechanical stress as possible must be applied to the fibres during predehydrating. Predehydrating can take place under application of compressed air, for example, and drying under application of tunnel dryers, for example, although other suitable processes and equipment known to the specialist can also be employed.

Under application of the invention-design process, a fibre is yielded which contains practically no more lignin and which is substantially free from sulphuric acid and carbon disulphide. Because of its lamellar microstructure, this fibre has an extremely large surface area. It is impossible to obtain such a large surface area with conventional fibres made from sulphite cellulose, because the sulphite pulping process leads to destruction of the lamellar structure.

The fibre produced in this manner has a preferred count of 330 dtex or more.

The fibre produced as described above can be used to manufacture a fabric which is characterised by a high absorptive capacity, good liquid-retention properties, high grease-solvent properties as well as particle-absorbing properties.

The invention-design fabric comprises a backing fabric and a pile woven into the backing fabric which contains the fibres manufactured in the manner described above.

The backing fabric preferably has a lattice-like structure. The backing fabric and pile can consist of the same type of fibre, although this is not essential. Durability criteria can make it necessary to use stronger backing fabric fibres, for example. The backing fabric preferably contains some viscose staple fibres; a backing fabric which consists exclusively of such fibres is ideal.

In a preferred invention design, the pile forms a fibre bed of approx. 0.5 cm in height above the backing fabric. The pile should preferably contain oval or tape fibres or a mixture of the two. A fabric whose pile contains a lot of oval fibres but only a small amount of tape fibres has especially high grease-adsorptive properties. A fabric whose pile contains a small amount of oval fibres but a lot of tape fibres is particularly suitable for reducing the surface tension of water.

Figure 16:
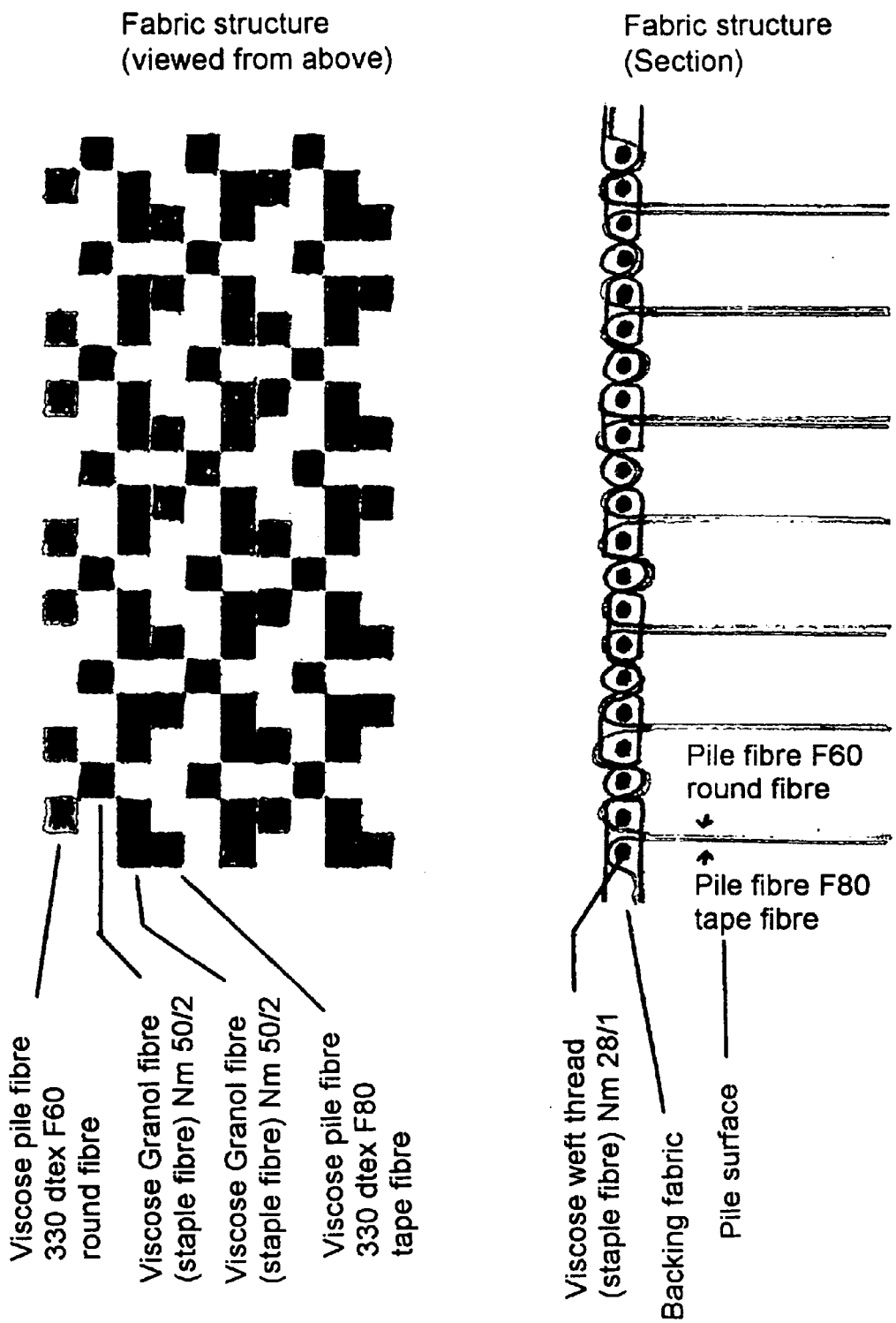
FIG. 16 shows an example of the invention-design fabric.
Figure 17:
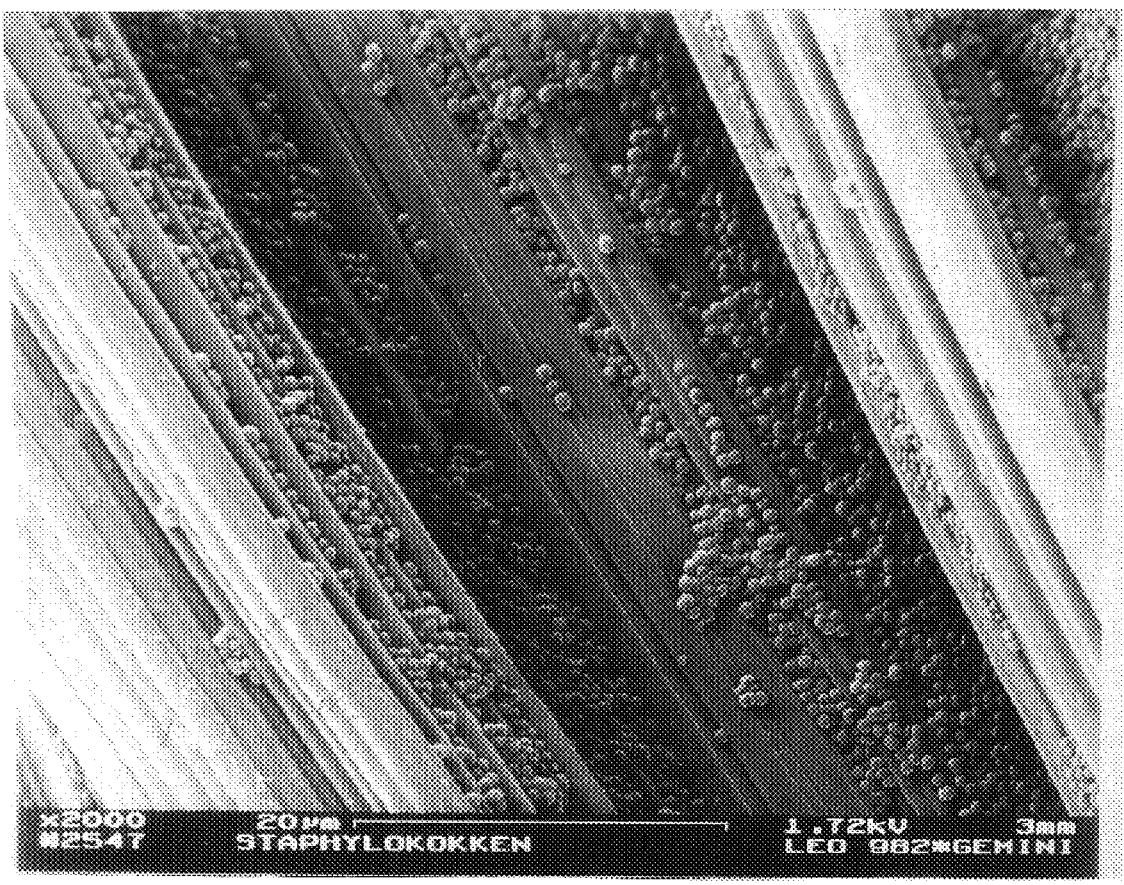
FIGS. 17 to 20 show electron micrographs of bacteria which are adsorbed on the lamellae of the invention-design fibres.
Figure 18:
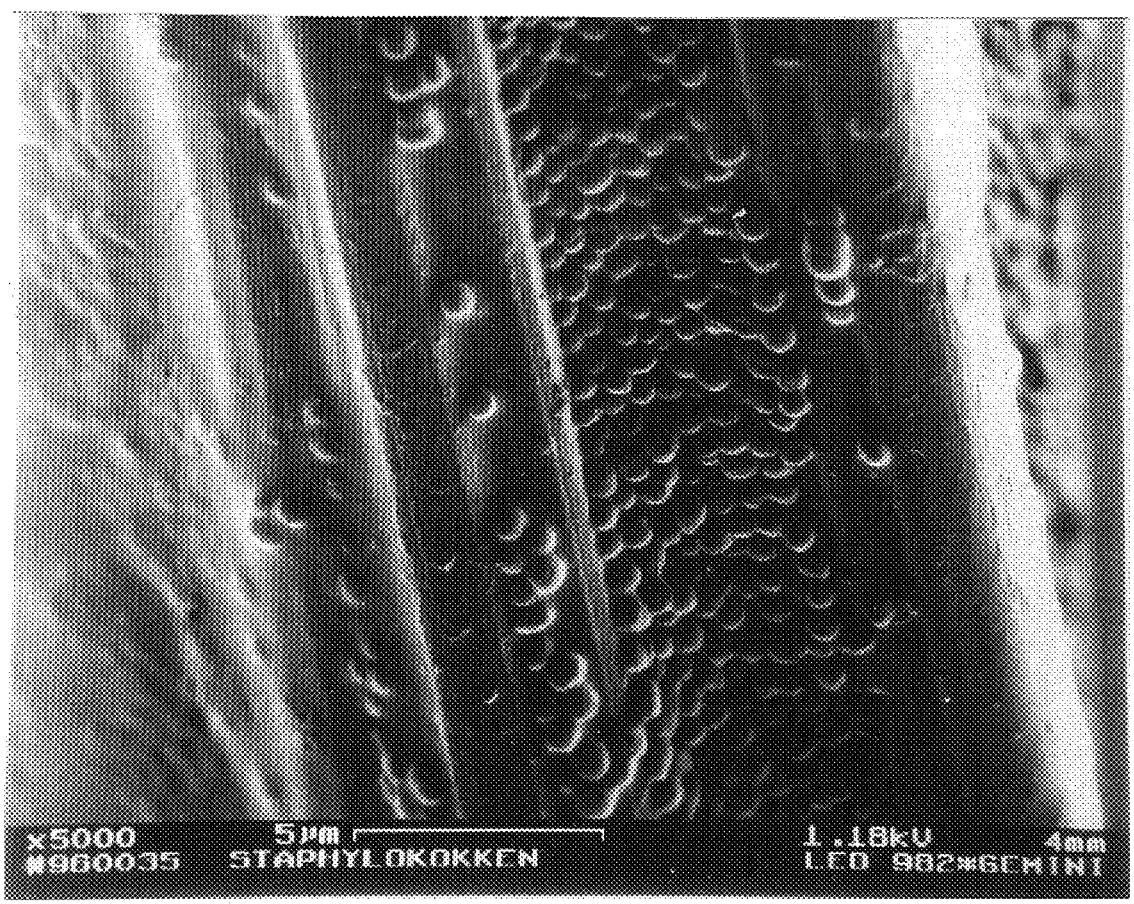
Figure 19:
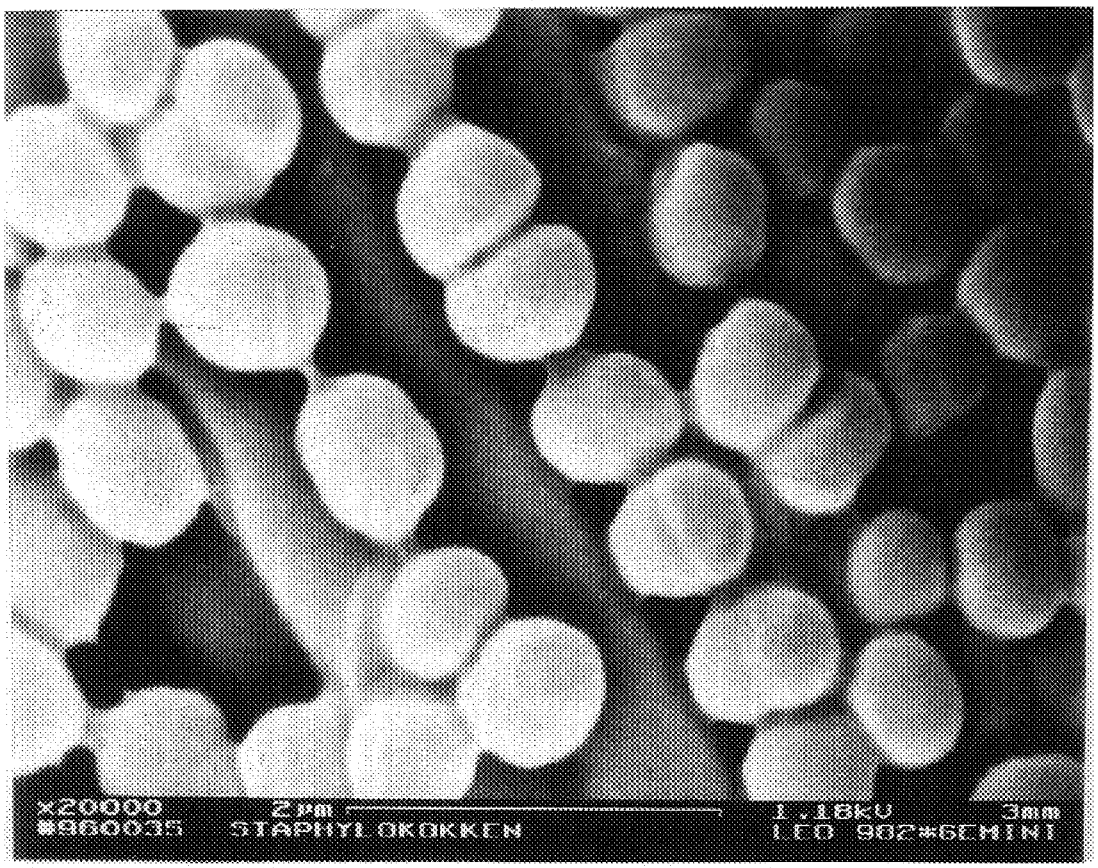
Figure 20:
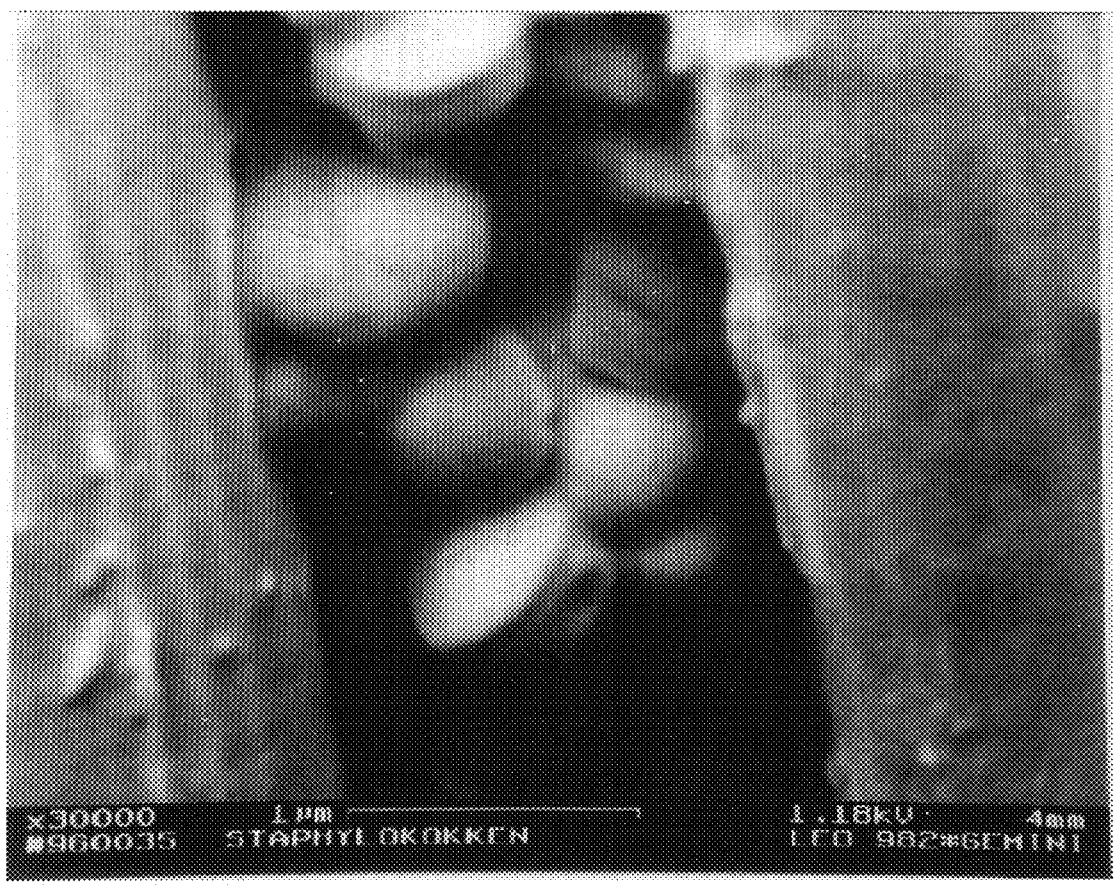

In another preferred invention design, the pile consists of 50% oval and 50% tape fibres. And in a particularly preferred invention design, the pile consists of 50% of oval fibres with a count of 330 dtex F60 and 50% of tape fibres with a count of 330 dtex F80. Such a fabric is shown in FIG. 16.

The invention-design fabric is characterised especially by the following properties:

it can bind bacteria and particles of dirt reversibly and can then be cleaned without the use of chemicals;

it has an extremely large specific surface area;

it has high specific fluid-retention properties; and it can be disposed of with minimum environmental impact.

The above-described properties give rise to a wide range of applications for the invention-design fabric.

Because the invention-design fabric is pH neutral, it can, for example, be used to manufacture personal hygiene articles which are kind to the skin, e.g. sanitary pads, as well as wash cloths to clean the body and skin, and especially to clean mucous membrane (stoma cleaning), and also to clean the skin if skin infections and neurodermatitis are a problem or as a wash cloth on the sector of personal hygiene for the aged and infirm. When using the fabric as a wash cloth, the skin surface can be cleaned of water-soluble and greasy cosmetics in an allergy-free and pH-neutral manner without the need of special cleansing agents. The fabric itself can then be cleaned of bacteria and cosmetics by simple mechanical cleaning (rinsing and wringing out) in cold water. This aspect gains particular significance if the skin is sensitive or damaged, e.g. as is the case with neurodermatitis or acne. Use of the invention-design fabric with nothing else bar water eliminates the possibility of additional skin irritation or damage. Germs, for example, can thus be removed from the skin more gently than with detergent surfactants or disinfectants.

The invention-design fabric can also be used as an udder cloth to clean and decontaminate cow's udders before connection to a milking machine. This rules out the possibility of germs being introduced into the milk.

On the other hand, the invention-design fabric can also be used to manufacture products which are themselves easy to clean, e.g. textiles and fabric for clothing; such products can then be cleaned without the need for any chemicals even if strongly soiled by foodstuff residues, etc. Examples of such products are bed linen, table linen, work clothes or baby articles (e.g. nappies, bibs and wash cloths), upholstery coverings for furniture or car seats as well as covering fabrics for stuffed toys. Stains left by ketchup, juice, red wine, lipstick or blood, to name just a few examples, can be removed from these products without residue by simple rinsing in cold water. Products such as nappies, wash cloths or bibs can also be washed residue-free without the need for washing detergents at temperatures of up to 40° C. It is also possible to wash the products in a washing machine either on a cold cycle or one up to 40° C. without the need for any washing detergents. The products can then be simply hung up to dry or can be dried in a dryer (up to 40° C.).

Another application for the invention-design fabric is the employment as a floor covering for special-purpose rooms (e.g. humid rooms) or hygienically sensitive rooms.

The invention-design fabric can also be used as a condensation catalyst to condense steam or humidity, e.g. as a "roof panel" for shower or bath cabins or humid rooms. The moisture is absorbed by the covering and then—during the course of a slow drying process—is released into the atmosphere again in a retarded manner. This prevents the rapid condensation of steam or moisture on the room walls, even if the room in question is badly ventilated (e.g. as in old buildings). The covering made from the invention-design fabric remains free from fungi, bacteria and algae.

Another possible application for the invention-design fabric is the use as a particle filter, e.g. to remove particles or micro-organisms from organic and inorganic fluids. To this end, the fabric can be layered in parallel layers, for example, or rolled.

The biophysical properties of the invention-design fabric are a result of the lamellar microstructure of the fibres on the one hand, and of the configuration of the fibres on the surface of the fabric on the other hand.

The following is a description of the employment of the invention-design fabric for cleaning and decontamination. This application permits organic surfaces (e.g. skin) or inorganic surfaces (e.g. objects, floors and windows) to be cleaned and the bacteria present on these surfaces to be removed without the need for disinfectants, meaning that the surfaces being cleaned are subject to neither chemical nor thermal stress. In contrast to conventional decontamination with disinfectants, decontamination with the invention-design fabric achieves the same or better germicidal effects without any selective processes caused by resistance to chemical attack occurring.

The invention-design fabric is wetted with water so that a certain residual moisture content (e.g. approx. 20%) remains. At this degree of residual moisture, the surface to be decontaminated can be mechanically decontaminated, whereby the ability of the fabric to reduce the surface tension of water leads to an improved lipid solubility. With a fabric measuring approx. 600 cm$^2$ in surface area, a highly contaminated surface of 1 m$^2$ can be cleaned optimally. The fabric itself is subsequently decontaminated by being steeped in water and moved to and fro mechanically. This type of cleaning serves to completely decontaminate the fabric, whereby every single contaminated particle is released into the water. The fabric itself remains biologically and chemically inert during this process. In the case of a surface to be cleaned of approx. 30 m², a contamination saturation of the cleaning water is reached at about 10 liters of water, although this is dependent on the degree of contamination of the surface. The adsorptive effect which exists when the fabric contains approx. 20% residual moisture is preserved for future cleaning procedures provided that no impermissible chemical, mechanical or thermal stresses destroy the fibre structure. The optimum temperature range for use of the fabric lies between 5 and 30° C. The adsorptive effect is destroyed as soon as the temperature exceeds 60° C. Intensive contact (impregnation) with detergents destroys the function of the fabric because it damages the surface structure. Contact with 0.1 standard acids or alkaline solutions or with alcoholic solutions presents no problem.

FIGS. 17 to 20 show electron micrographs (magnified 2,000, 5,000, 20,000 and 30,000 times) of bacteria (here: staphylococci) which are adsorbed on the lamellae of the invention-design fibres.

Surprisingly, it turned out that the invention-design fabric was also capable of reducing the surface tension of water by as much as 20% or more without the use of any chemicals. Water of this nature with a reduced surface tension can be used for extraction processes or synthesis as well as for fermentation processes—for example in brewing operations.

To achieve a reduction of the surface tension, the water is brought into contact with the invention-design fabric. The effect manifests itself within a short time, is practically independent of the water temperature and lasts for about two hours.

Figure 21:
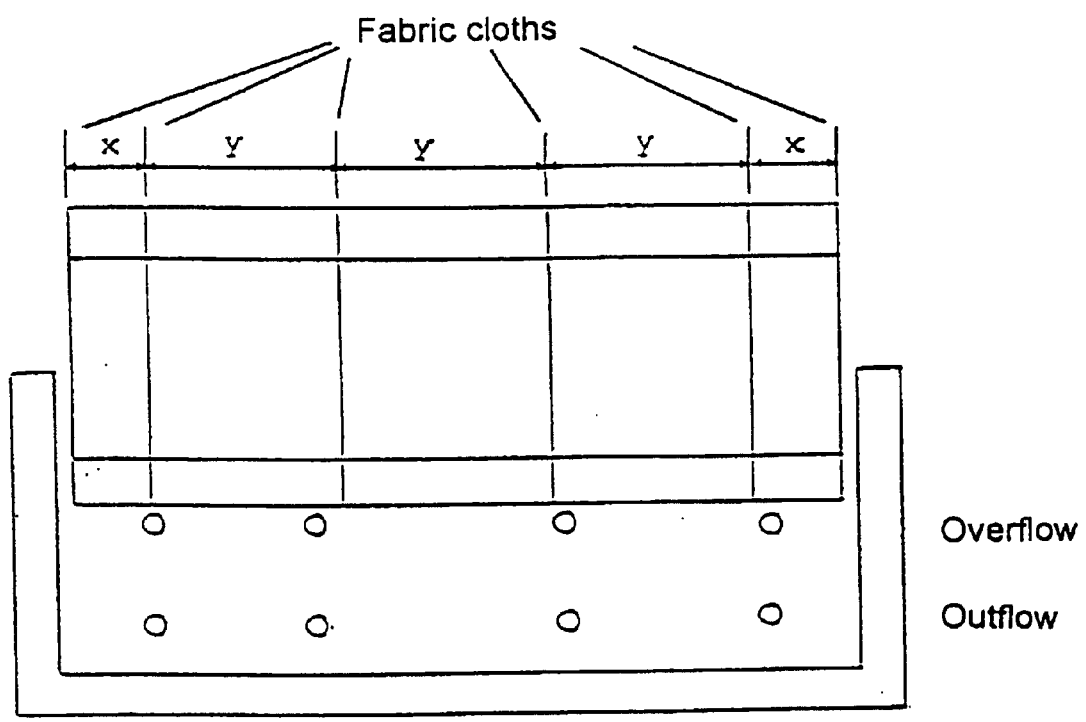
FIG. 21 shows a device to obtain water with a reduced surface tension.

FIG. 21 shows a device to obtain water with a reduced surface tension. The device comprises, e.g. a vessel filled with water which is equipped with an overflow and an outflow. Several invention-design fabrics can be put into the vessel simultaneously.

The following examples and the figures illustrate the invention.

EXAMPLE 1
Fabric for Cleaning Contaminated Surfaces
Test-rig Configuration
1.1 Tested Bacterial Strains
  E. coli
  Staphylococcus aureus
  Streptococcus pyogenes
  Enterococci (S. faecium)
  Streptococcus bovis
  Pseudomonas pyocyanea
1.2 Cultures
  Cultures prepared by means of incubation in nutrient broth or litmus milk (mixture of litmus and milk) or in nutrient agar at between 25 and 30° C. until the bacterial count reaches >10⁶ bacteria/ml. The number of bacteria was determined (corresponds to the primary bacterial count= 100%).
1.3 Test Procedure
  The fabric was immersed in the above-described medium with a bacterial concentration >10⁶ bacteria/ml for a period of 15 minutes. The fabric was then placed (not rinsed) in lukewarm water (10–20° C.) for between 1 and 3 minutes. It was then removed from the water and put into a sterile nutrient solution, which was then incubated. The bacterial concentration in the nutrient solution was determined after a period of between 24 and 72 hours. The measured values were related to the primary bacterial count, whereby the following results were achieved:

|  | I | II | III |
|---|---|---|---|
| E. coli | 15% | 12% | 9% |
| Staph. aureus | 18% | 16% | 16% |
| Strept. pyogenes | 5% | 6% | 4% |
| Enterococci | 7% | 5% | 8% |
| Strept. bovis | 17% | 12% | 14% |
| Pseudom. pyogenes | 6% | 4% | 3% |

Subsequent to re-incubation, the measured bacterial densities/concentrations of all bacterial strains reduced markedly.

EXAMPLE 2
Germicidal Properties of the Invention-design Fabric Used to Clean the Udders of Dairy Cows The tests were carried out on 5 cows each in 3 dairy farms during 10 milking periods. One half of the cows' udders was cleaned with the cloth the farm normally used and then soaked in disinfectant, whereas the other half was cleaned with the invention-design fabric. The udder halves were changed at every milking time. After cleaning, the invention-design fabric was placed in water with no detergents or disinfectants. The comparison cloths were also placed in water, whereby on one farm, a disinfectant was added to the water. Before and after the udder cleaning, an impression culture was prepared on ass, agar (antibiotic sulphonamide sensitivity agar) from each cloth and was incubated for 18 hours at between 38 and 40° C.

Results

In differentiating the bacteria by means of selective cultures, it was predominantly the following bacteria which were found:
  E. coli
  Streptococci
  Staphylococci
  Enterococci Assuming the primary bacterial count to be 100%, we arrived at the following values:

|  | Invention-design fabric | Farm's own cleaning cloth | |
|---|---|---|---|
|  |  | without disinfectant | with disinfectant |
| E. coli | 10% | 92% | 35% |
| Streptococci | 3% | 87% | 25% |
| Staphylococci | 2% | 78% | 20% |
| Enterococci | 9% | 83% | 41% |

The statistical evaluation of the results clearly shows the germicidal property of the invention-design fabric. In other words, the risk of transferring germs from one cow to another during milking is significantly reduced with the invention-design fabric.

EXAMPLE 3

Cleaning a Contaminated Invention-design Fabric—Comparison with a Conventional Cotton Fabric The invention-design fabric was cut into squares measuring 6×6 cm which were then used to wipe contaminated surfaces. The comparison fabric—a cotton fabric which had been washed several times—was also cut into pieces of about the same weight (see Tables 2–6). The test surfaces consisted of glazed ceramic tiles (5×5 cm) which had been inoculated with one of the test bacterial strains, i.e. either *Enterococcus faecium, Escherichia coli* or *Staphylococcus aureus*. The tiles were each inoculated with 50 μl of an overnight culture of the test bacteria, so that the number of bacteria to be recovered from the tiles was between $3.4 \times 10^5$ and $8.9 \times 10^6$. The contamination degree of the test surfaces was controlled in two ways: the bacterial count was determined in the inoculation suspension; and the inoculated surfaces were rinsed, dried and then analysed. Drying took place by means of a 20-minute exposure at approx. 25° C. in a laminar flow workbench. The surfaces were then wiped with the test fabrics and the bacterial count on the tiles was determined by rinsing the tiles in 100 ml of sterile, distilled water and by distributing some of the rinsing solution on nutrient agar slides with a spatula. The number of bacteria taken up from the tiles into the test fabrics was also determined by rinsing at room temperature in 200 ml of distilled water, this process being assisted mechanically by manually wringing the fabrics out, and the rinsing solution was then inoculated onto nutrient agar slides. The number of bacteria remaining in the test fabrics after rinsing was determined by means of a second rinse, and in the last test series by means of a third rinse. The following tables therefore show the bacterial counts of the following suspensions:

Overnight culture (inoculation suspension)
Rinsing water used to rinse the inoculated surface
Rinsing water used to wipe the surface
Rinsing water from the fabric after wiping the tiles
Rinsing water from the fabric after the first rinse
Rinsing water from the fabric after the second rinse The test results are summarised in the following tables. Table 2: *E. coli* ATCC 11229; Table 3: *Enterococcus faecium;* Table 4: *Enterococcus faecium;* Table 5: *Staphylococcus aureus* ATCC 6538; and Table 6: tests with all three test bacteria. The test parameters applied for Tables 2 to 5 were more or less identical. The difference between Tables 3 and 4 (both with *Enterococcus faecium*) is the lower localised propagation on the inoculated surfaces. In Table 6, both the test fabric and the control fabric were rinsed once again to determine whether this made any difference to the bacterial count in the fabric over that of a fabric which had been rinsed only once.

TABLE 2

Bacteria: *E. coli* ATCC 11229

Inoculation with overnight culture KBE/50 μl

| | I | | II | | III | |
| | *E. coli* $2.6 \times 10^6$ on tile | | *E. coli* $1.4 \times 10^7$ on tile | | *E. coli* $3.0 \times 10^7$ on tile | |
| Measured bacterial count | Invention-design fabric | Cotton | Invention-design fabric | Cotton | Invention-design fabric | Cotton |
| --- | --- | --- | --- | --- | --- | --- |
| on inoculated surface | $5.6 \times 10^5$ | $5.6 \times 10^5$ | $3.7 \times 10^5$ | $3.7 \times 10^5$ | $3.4 \times 10^5$ | $3.4 \times 10^5$ |
| in fabric after wiping surface | $4.8 \times 10^5$ | $4.0 \times 10^5$ | $3.8 \times 10^5$ | $3.0 \times 10^5$ | $5.8 \times 10^5$ | $1.8 \times 10^5$ |
| in fabric after rinsing | $7.0 \times 10^3$ | $6.0 \times 10^3$ | $3.0 \times 10^3$ | $6.0 \times 10^3$ | $5.0 \times 10^3$ | $4.0 \times 10^3$ |
| on tile after wiping | $1.2 \times 10^4$ | $2.3 \times 10^4$ | 0.0 | $6.5 \times 10^3$ | $3.6 \times 10^4$ | $6.0 \times 10^3$ |
| weight 6 × 6 cm in g | 1.941 | | 1.998 | 0.875 | 2.106 | 1.951 |

TABLE 3

Bacteria: *Enterococcus faecium*

Inoculation with overnight culture KBE/50 μl

| | I | | II | | |
| | $2.0 \times 10^7$ on tile | | $2.1 \times 10^7$ on tile | | |
| Measured bacterial count | Invention-design fabric | Cotton | Invention-design fabric | Invention-design fabric | Cotton |
| --- | --- | --- | --- | --- | --- |
| on inoculated surface | $4.8 \times 10^5$ | $4.8 \times 10^5$ | $6.0 \times 10^5$ | $6.0 \times 10^5$ | $6.0 \times 10^5$ |
| in fabric after wiping surface | $3.6 \times 10^5$ | $3.2 \times 10^5$ | $5.0 \times 10^5$ | $4.0 \times 10^5$ | $1.8 \times 10^5$ |
| in fabric after rinsing | $2.0 \times 10^3$ | $5.0 \times 10^3$ | $4.0 \times 10^3$ | $3.0 \times 10^3$ | $2.0 \times 10^3$ |
| on tile after wiping | $3.0 \times 10^3$ | $1.0 \times 10^4$ | $5.0 \times 10^3$ | $4.0 \times 10^3$ | $3.0 \times 10^3$ |
| Weight 6 × 6 cm in g | 1.679 | 1.017 | 1.852 | 1.784 | 0.950 |
| Initial germination of cloth | $1.0 \times 10^3$ | | $3.0 \times 10^3$ | $3.0 \times 10^3$ | |

TABLE 4

Bacteria: *Enterococcus faecium*

Inoculation with overnight culture KBE/50 μl

| | III $1.8 \times 10^7$ on tile | | | IV $3.0 \times 10^7$ on tile | |
|---|---|---|---|---|---|
| Measured bacterial count | Invention-design fabric | Invention-design fabric | Cotton | Invention-design fabric | Cotton |
| on inoculated surface | $8.9 \times 10^6$ | $4.9 \times 10^5$ | $8.9 \times 10^6$ | $6.7 \times 10^5$ | $6.7 \times 10^5$ |
| in fabric after wiping surface | $6.2 \times 10^6$ | $2.6 \times 10^5$ | $4.8 \times 10^5$ | $6.0 \times 10^5$ | $4.6 \times 10^5$ |
| in fabric after rinsing | $7.9 \times 10^4$ | $5.0 \times 10^3$ | $3.6 \times 10^4$ | $2.0 \times 10^3$ | $6.0 \times 10^3$ |
| on tile after wiping | $7.1 \times 10^4$ | $5.0 \times 10^3$ | $5.6 \times 10^4$ | $7.5 \times 10^3$ | $5.5 \times 10^3$ |
| Weight 6 × 6 cm in g | 1.948 | 1.765 | 0.775 | 2.059 | 1.968 |
| Initial germination of cloth | $2.0 \times 10^3$ | $4.0 \times 10^3$ | | | |

TABLE 5

Bacteria: *Staphylococcus aureus* ATCC 6538

Inoculation with overnight culture KBE/50 μl

| | I Staph. aureus $7.5 \times 10^7$ on tile | | II Staph. aureus $4.0 \times 10^7$ on tile | | III Staph. aureus $6.0 \times 10^7$ on tile | |
|---|---|---|---|---|---|---|
| Measured bacterial count | Invention-design fabric | Cotton | Invention-design fabric | Cotton | Invention-design fabric | Cotton |
| on inoculated surface | $4.8 \times 10^6$ | $4.8 \times 10^6$ | $2.3 \times 10^6$ | $2.3 \times 10^6$ | $7.0 \times 10^6$ | $7.0 \times 10^6$ |
| in fabric after wiping surface | $4.6 \times 10^6$ | $1.1 \times 10^6$ | $1.6 \times 10^6$ | $1.0 \times 10^5$ | $7.0 \times 10^6$ | $5.0 \times 10^6$ |
| in fabric after rinsing | $6.6 \times 10^4$ | $5.0 \times 10^2$ | $1.6 \times 10^4$ | 0.0 | $9.0 \times 10^4$ | $1.3 \times 10^5$ |
| on tile after wiping | $1.9 \times 10^5$ | $6.0 \times 10^4$ | $6.4 \times 10^4$ | $1.4 \times 10^4$ | $7.4 \times 10^4$ | $7.5 \times 10^4$ |
| Weight 6 × 6 cm in g | 1.987 | | 1.855 | 0.960 | 1.939 | 1.937 |

TABLE 6

Inoculation with overnight culture KBE/50 μl

| | E. faecium $3.9 \times 10^7$ on tile | | E. coli $3.8 \times 10^7$ on tile | | Staph. aureus $6.0 \times 10^7$ on tile | |
|---|---|---|---|---|---|---|
| Measured bacterial count | Invention-design fabric | Cotton | Invention-design fabric | Cotton | Invention-design fabric | Cotton |
| on inoculated surface | $1.0 \times 10^6$ | $1.0 \times 10^6$ | $3.8 \times 10^5$ | $3.8 \times 10^5$ | $6.8 \times 10^6$ | $6.8 \times 10^6$ |
| in fabric after wiping surface | $4.6 \times 10^5$ | $5.0 \times 10^5$ | $3.8 \times 10^5$ | $4.4 \times 10^5$ | $5.0 \times 10^6$ | $2.6 \times 10^6$ |
| in fabric after rinsing once | $8.0 \times 10^3$ | $1.0 \times 10^4$ | $7.2 \times 10^3$ | $8.8 \times 10^3$ | $4.6 \times 10^4$ | $1.4 \times 10^5$ |
| on tile after wiping | $6.0 \times 10^2$ | $3.3 \times 10^3$ | $1.5 \times 10^3$ | $5.2 \times 10^3$ | $7.8 \times 10^4$ | $1.0 \times 10^5$ |
| in fabric after rinsing twice | $6.0 \times 10^1$ | $8.4 \times 10^2$ | $2.0 \times 10^2$ | $6.8 \times 10^2$ | $6.0 \times 10^2$ | $4.4 \times 10^3$ |
| Weight 6 × 6 cm in g | 1.933 | 2.0 | 2.034 | 2.0 | 2.015 | 2.0 |

The quantitative evaluation of the test results shows that the tiles are cleaned to more or less the same degree by both the invention-design fabric and the cotton fabric. Although there are only signs that the invention-design fabric has a better cleaning effect, a distinct difference can be seen in the measured bacterial count in the fabrics after use. At this point, a greater number of the micro-organisms remain in the invention-design fabric than in the cotton fabric. After the first rinse, the bacterial counts in both fabrics are more or less the same, but after the second rinse (Table 6), the bacterial count in the invention-design fabric is below that of the cotton fabric in all three analyses.

The results show that the invention-design fabric can be freed of the absorbed bacteria by simple rinsing in pure water better than the conventional cotton fabric, and that it is superior to the cotton fabric when it comes to cleaning the surfaces. The invention-design fabric is therefore especially suitable for cleaning surfaces and for other applications where a reversible absorption of bacteria is required.

EXAMPLE 4

Preparation of Water with a Reduced Surface Tension

To demonstrate the preparation of water with a reduced surface tension, fresh tap water with a hardness degree of between 5 and 25 and any mixture of ions is preferred; the process can be carried out within a preferred temperature range of between 5 and 30° C., or ideally between 15 and 25° C., and leads to water with a distinctly reduced surface tension. It is preferable to use a container with a completely smooth surface, e.g. of glass, metal, enamel or ceramic, in which the water can make contact with the invention-design fabric.

The invention-design fibre should preferably be woven into a double-sided fabric with a bed of fibres on each side which are 0.5 cm in length. Assuming this and the fact that the cloths are spaced in water at uniform intervals, a surface area of 1 m² of fabric with double-sided pile for 0.16 m³ of water at a residence time of between 5 and 10 seconds is required for an optimal degree of surface-tension reduction. The water vessel used can be any shape. The fabric can be clamped in place in a basin or if preferred, suitable mechanical means can be employed to dip the fabric into a basin. After the fabric is removed from the vessel or the water is removed from the vessel, the water retains its reduced surface tension at temperatures of up to 40° C. for at least 60 minutes, whereas the surface tension gradually rises again to normal values (72 to 78 mN/m) after 120 minutes. During this time, the water can be integrated into synthesis, extraction or fermentation processes, both with or without fibre contact. Whereby it is also possible, for example, to introduce the water at all fermentation stages—even at temperatures of above 40° C.—in order to improve and accelerate the fermentation processes during brewing.

In the same way, it is also possible after the mash has cooled and before the yeast has been added to reduce the surface tension by means of the dipping method in order to achieve better brewing results.

EXAMPLE 4.1

In this example, 3 invention-design fabric samples "S10", "L01", and "L02" were investigated, samples which differ in terms of their surface structure quality.

The measurements were made in glass vessels, whereby an effective surface area of the fabric samples measuring 400 cm² was analysed in 4 liters of water. The temperature during the tests was around 20° C.

The measurements were carried out
1. without previous rinsing
2. after three rinses
3. after six rinses
4. after nine rinses
of the respective fabric sample.

The comparison measurements were carried out in bidistilled water and in fresh water taken from the tap.

Figure 22:
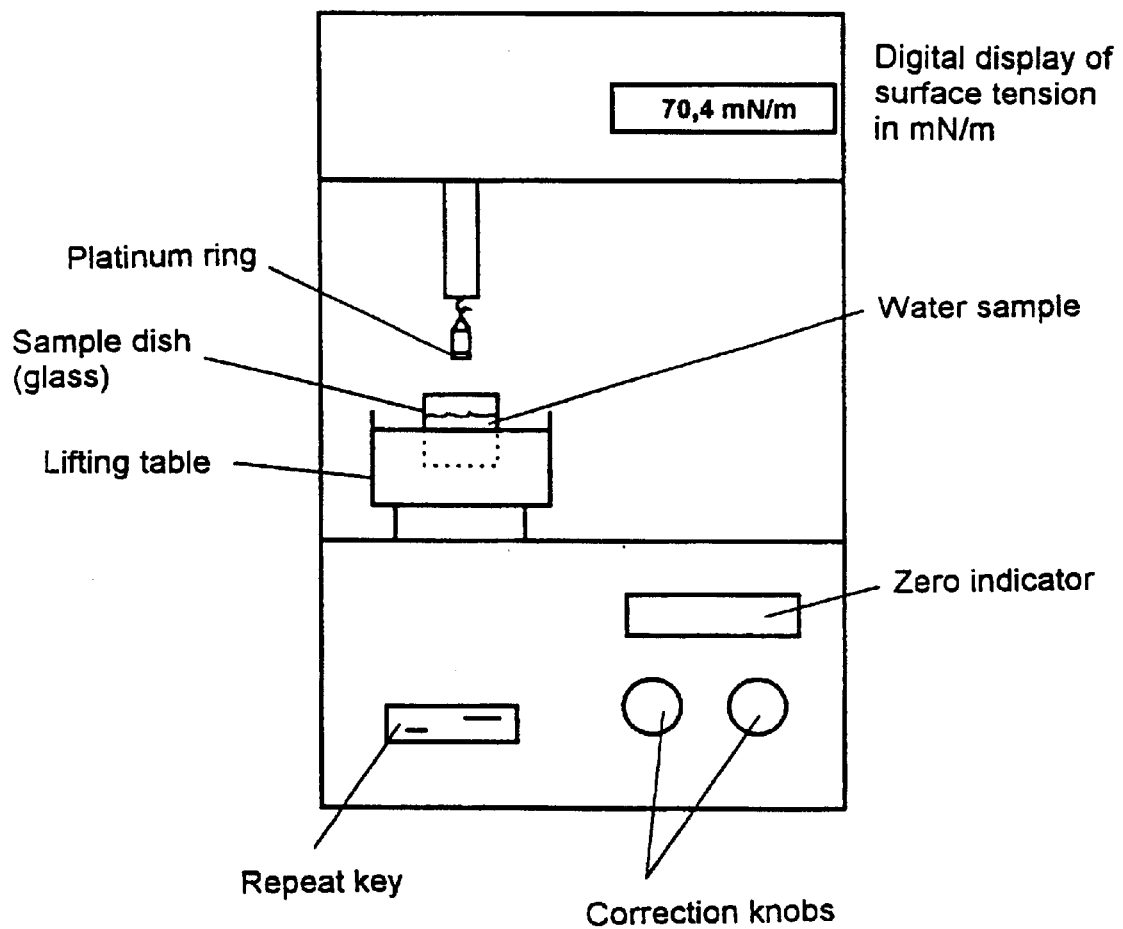
FIG. 22 shows a tensiometer to measure the surface tension.

The surface tension was measured with the tensiometer shown in FIG. 22.

Test Description

A 5-liter vessel of Duran glass is filled with 4 liters of fresh tap water of 20° C., and a sample of this water is extracted to measure the surface tension. The test fabric is then immersed in the water, kneaded a few times and then removed after being wrung out. Several samples are taken of the water remaining in the glass vessel, and the surface tension is measured. In the same way as described above, the fabric is now rinsed twice without subsequent measurement in two lots of fresh water measuring 4 liters each. The entire process is repeated three times.

The surface tension is measured as follows: The water sample is filled into the sample dish of the tensiometer and the dish is then placed on the lifting table and raised until the platinum ring immerses in the sample. The servomotor is then activated which lowers the water sample on the table, whereby a water leaf at the ring is extracted. The motor stops at maximum stress as soon as the surface film starts to give and there is no more tensile load acting on the balance from which the ring is suspended. The maximum value can be read off the digital display.

One-sided Fabric

First of all, the effect of one-sided fabric samples of 400 cm² in size is investigated. To this end, each fabric sample is placed in 4 liters of fresh water of 20° C. and removed after being stirred several times in the water. This takes place initially with unrinsed fabrics. A sample is then extracted and the surface tension measured.

The fabric is then rinsed three times and the test repeated. The test is also repeated after each fabric has been rinsed six times and nine times.

Figure 23:
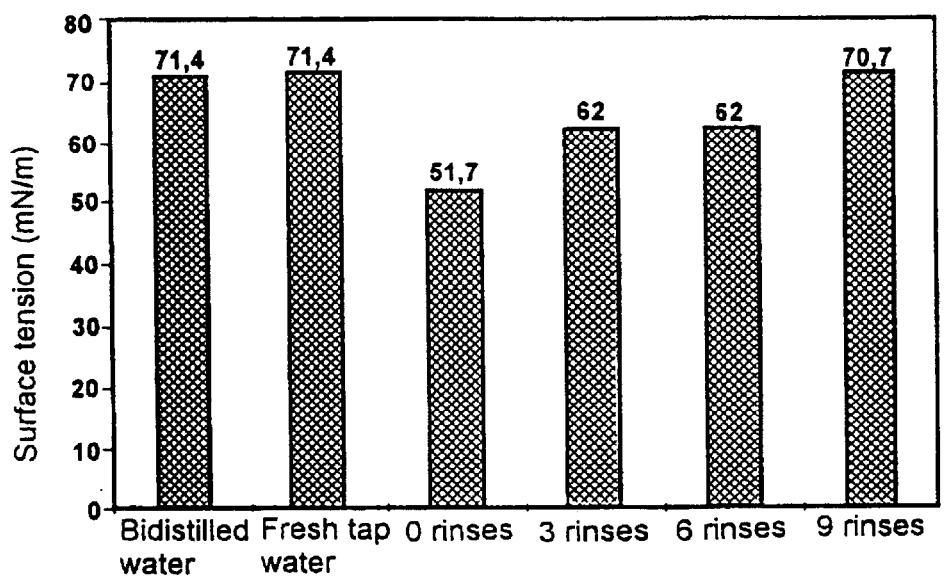
FIGS. 23 to 28 show the surface tension-reducing effect of invention-design fabrics as a function of rinsing the fabric.
Figure 24:
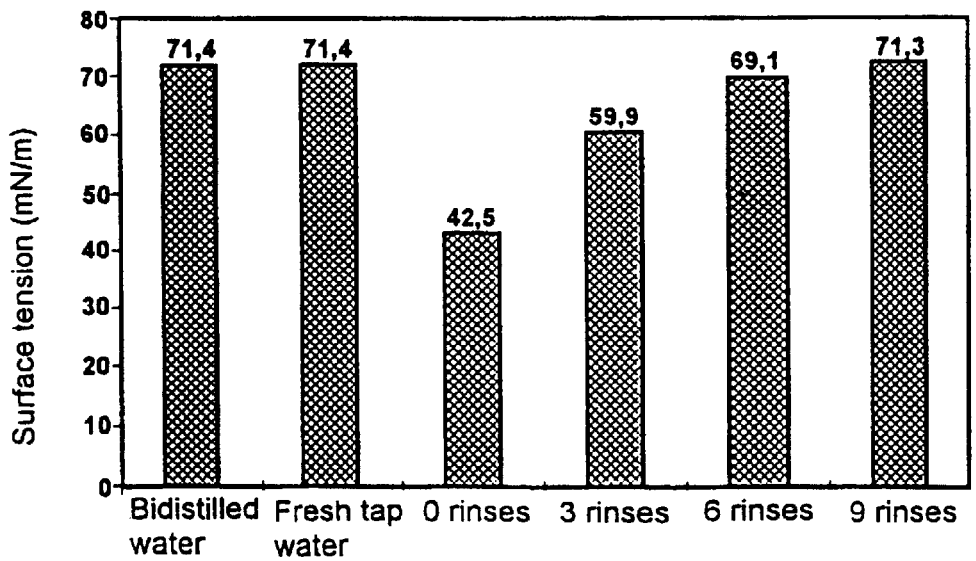
Figure 25:
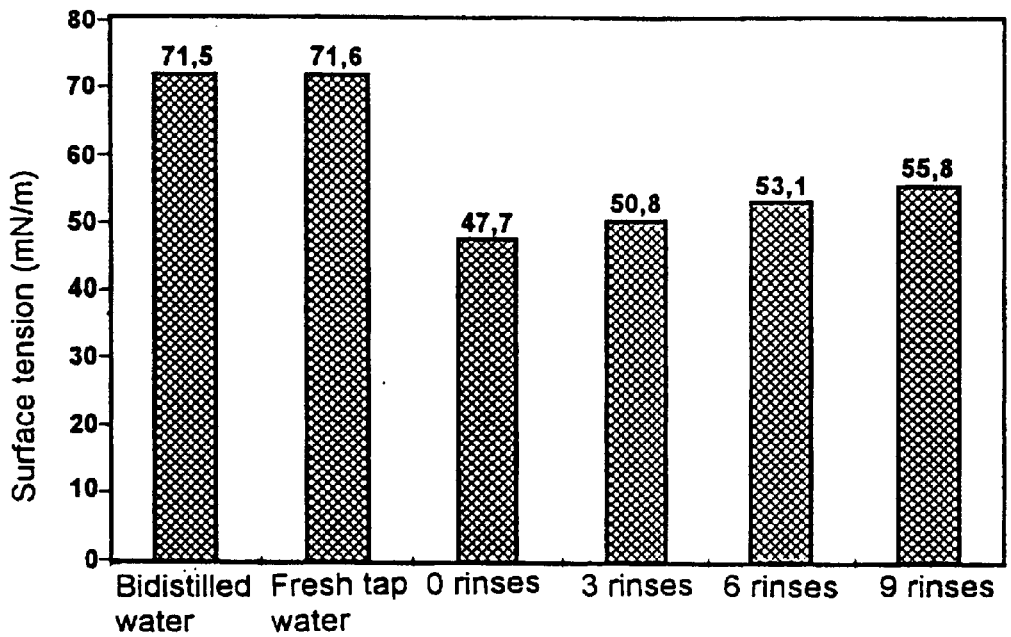

FIGS. 23 to 25 show the surface tension values measured after zero, three, six and nine rinses plotted against those of bidistilled water and fresh water. In the case of all rinses, a high introduction of air into the test water was observed, as well as "fuzzing", which caused the measured values to fluctuate. Because of this, several measurements were made and the arithmetic mean shown in each case.

In the case of FIGS. 23 to 25, the same statement in broad terms can be made: Immersing the respective fabric in the test water reduces the surface tension by 30–40%, from approx. 71 mN/m to 40–50 mN/m. The surface tension-reducing effect of the respective fabric decreases in proportion to the number of times the fabric is rinsed.

Double-sided Fabric

In comparison to the single-sided fabrics, the double-sided fabrics display more than double the mass at the same surface area of 400 cm². The measured values of each fabric are shown in Table 7.

TABLE 7

| | Mass of tested fabric | |
| --- | --- | --- |
| Type | One-sided | Double-sided |
| L01 | 16.10 g | 38.87 g |
| L02 | 16.69 g | 38.44 g |
| S10 | 15.53 g | 41.31 g |

Figure 26:
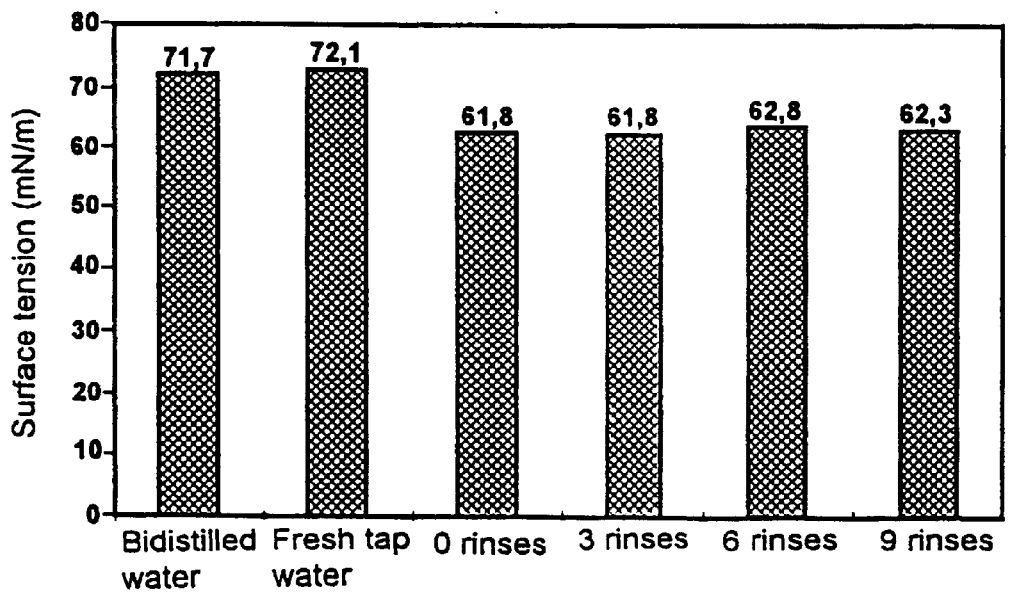
Figure 27:
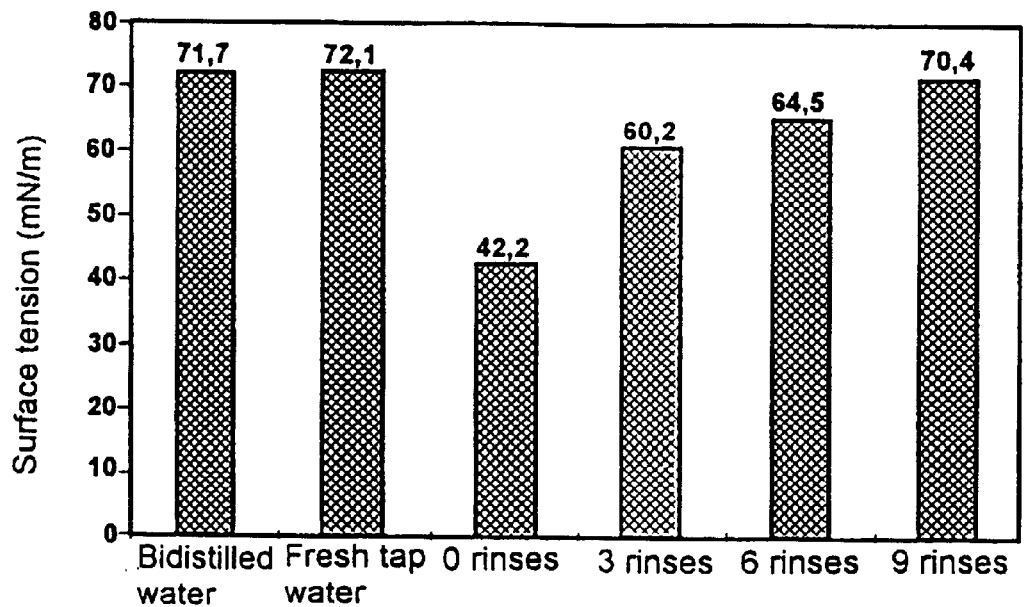
Figure 28:
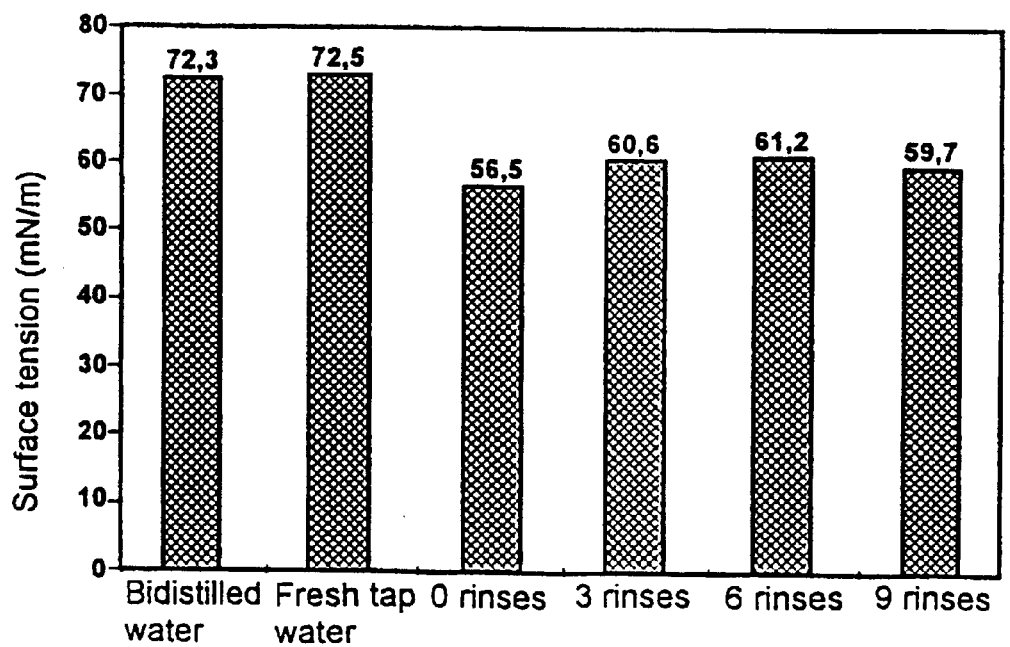

The surface tension-reducing effect of the double-sided fabric as a function of the number of rinses is shown in FIGS. 26 to 28.

The double-sided fabrics L01 and S10 reduce the surface tension of the sample from around 72 mN/m to 60–62 mN/m. This corresponds to a reduction of 14–17%. This effect is independent of the number of rinses and remains on the same level even after 9 rinses.

Initially, the double-sided fabric L02 succeeds in reducing the surface tension by 42%, from 72 mN/m to 42 mN/m. However, the surface tension-reducing effect decreases as the number of rinses increases, and final measurement after 9 rinses showed a value of 70.4 mN/m.

Figure 29:
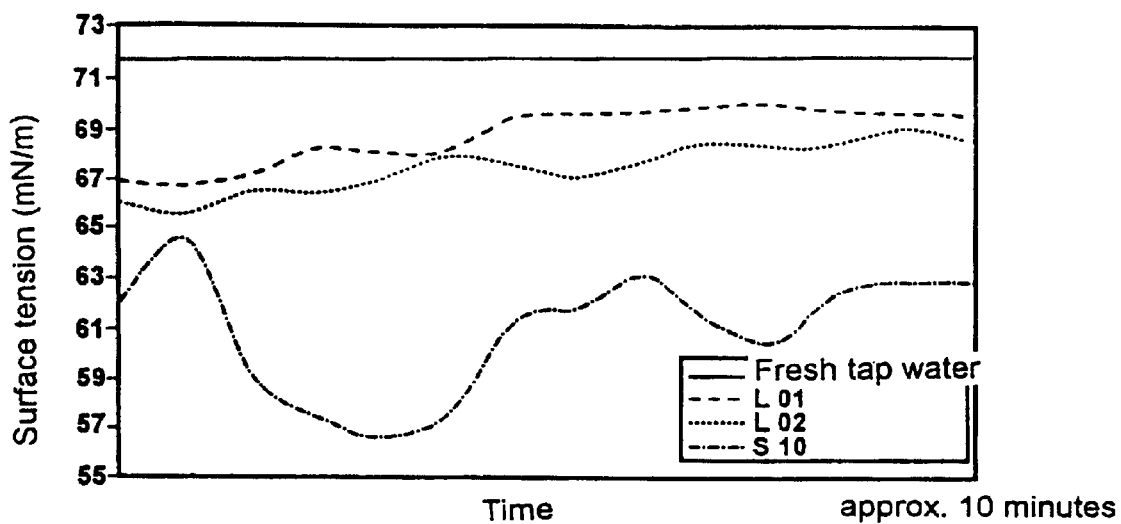
FIG. 29 shows the history of the surface tension in the case of fabrics which remain in the water.

Surface tension when fabrics remain in the water:

In this test, the respective fabrics were not removed from the water before measuring the surface tension. Several measurements were made one after the other in rapid succession. FIG. 29 shows the surface tension gradient of fabrics L01, L02, and S10 as a function of the time. A constant value did not set in until after about 10 minutes. The water temperature was a constant 20° C.

Whereas the value of the water with the fabrics L01 and L02 set in at between 69 and 68 mN/m, the water with the fabric S10 displays a distinctly lower final value of 62 mN/m.

In summarising, we can state that:

The first contact of the invention-design fabric with water succeeded in reducing the surface tension of fresh water by up to 40%, from approx. 72 mN/m to values around 40 mN/m. This effect, however, diminishes in the case of the one-sided fabrics in proportion to the number of rinses, as the repeated tests showed. In the case of the double-sided fabrics L01 and S10, these fabrics were each still able to reduce the surface tension of fresh water by 14–17% even after being rinsed nine times. A constant value set in here which differed only negligibly from the values measured after 3 and 6 rinses.

The double-sided fabric L02 behaved in an analogous way to the one-sided fabrics, where the surface tension-reducing effect diminished with increasing number of rinses.

If the fabrics are left in the water, a constant surface tension value of 62 mN/m sets in after about 10 minutes under ideal conditions. In comparison with fresh water (72 mN/m), this means a reduction of the surface tension by 14%.

EXAMPLE 4.2

In this test, the surface tension-reducing effect on water of the double-sided fabric L01 described in Example 4.1 after a drying phase of several months was tested.

The measurements were carried out in glass vessels. An effective surface area of 400 cm$^2$ of fabric was investigated in 4 liters of water. The temperature was 20° C.

The comparison measurements were carried out in bidistilled water and fresh tap water from the mains.

The surface tension was measured with the tensiometer shown in FIG. 22.

Test Description

A 5-liter vessel of Duran glass is filled with 4 liters of fresh tap water, and one with bidistilled water, whereby the temperature was 20° C. in each case, and a sample of water is extracted from each vessel to measure the surface tension. The test fabric is then immersed, kneaded a few times and removed after being wrung out. Several samples are taken of the water remaining in the glass vessels, and the surface tension is measured.

The surface tension is measured as follows: The water sample is filled into the sample dish of the tensiometer and the dish is then placed on the lifting table and raised until the platinum ring immerses in the sample. The servomotor is then activated which lowers the water sample on the table, whereby a water leaf at the ring is extracted. The motor stops at maximum stress as soon as the surface film starts to give and there is no more tensile load acting on the balance from which the ring is suspended. The maximum value can be read off the digital display.

Figure 30:
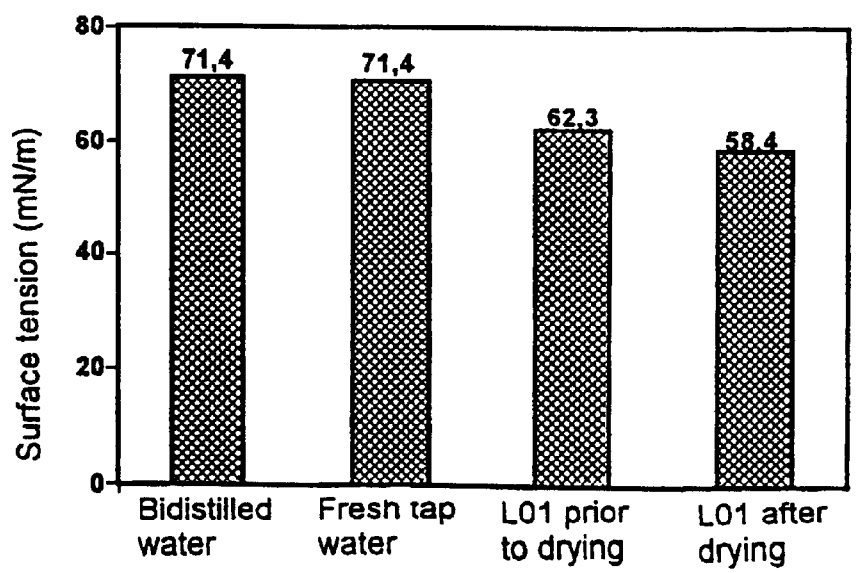
FIG. 30 shows the surface tension-reducing effect of the invention-design fabric before and after a drying phase.

FIG. 30 compares the surface tension of water after contact with fabric "L01" investigated both before and after the drying phase, as well as after contact with fresh tap water and bidistilled water. During measurement, it was registered that a large amount of air was introduced into the test water, which led to fluctuating values. Because of this, several measurements were made and the arithmetic mean show in each case. The individual measurements are shown in Table 8.

TABLE 8

Surface tension-reducing effect of the invention-design fabric "L01" before and after the drying phase (individual values).

| | Surface tension (mN/m) | |
|---|---|---|
| Single measurement | L01 prior to drying | L01 after drying |
| 1 | 62.0 | 58.2 |
| 2 | 62.4 | 58.4 |
| 3 | 62.5 | 58.3 |
| 4 | 62.1 | 58.4 |
| 5 | 62.5 | 58.7 |
| Mean value x | 62.3 | 58.4 |

The surface tension-reducing effect of the double-sided fabric "L01" did not deteriorate after the drying phase. It was still capable of reducing the surface tension from to 71.4 mN/m to 58.4 mN/m, i.e. by 18%.

This test shows that the surface tension-reducing effect of the invention-design fabric can be attributed to the fibre structure, and not to substances leached from the fabric. The surface tension-reducing effect is therefore retained even after a prolonged period of drying.

EXAMPLE 4.3

Tables 9 and 10 show results from other tests which were carried out. The fabrics were all rinsed once or twice with water before the test, in order to remove any impurities left over from the manufacturing process.

TABLE 9

Measuring results with different vessels

| Measurement No. | Vessel | Amount [litres] | Temperature [° C.] | Comments | Waiting time [min] | Surface tension before treatment [mN/m] | Surface tension after treatment [mN/m] |
|---|---|---|---|---|---|---|---|
| 1 | Glass | 4 | 17 | bidistilled water | 0 | 71.9/71.9 | — |
| 2 | Glass | 4 | 17 | tap water (TW) | 0 | 71.7/71.6 | — |
| 3 | Glass | 4 | 16 | TW + fabric (rinsed once) | 0 | 71.6 | 52.4 |
| 4 | Glass | 4 | 15 | TW + fabric (rinsed twice) | 0 | 72.2 | 52.5 |
| 5 | Plastic | 10 | 14 | TW + fabric (rinsed twice) | 0 | — | 65.4 |
| 6 | Glass | 4 | 13 | TW + fabric (rinsed twice) | 0 | — | 58.8 |
| 7 | Plastic | 4 | 14 | TW + fabric (rinsed twice) | 0 | 72.6 | 62.2 |
| 8 | Plastic | 10 | 14 | TW + fabric (rinsed twice) | 0 | 71.1 | 60.7 |

TABLE 10

Measuring results at different temperatures

| Measurement No. | Vessel | Amount [litres] | Temperature [° C.] | Comments | Waiting time [min] | Surface tension before treatment [mN/m] | Surface tension after treatment [mN/m] |
|---|---|---|---|---|---|---|---|
| 1 | Glass | 4 | 15 | TW + fabric | 0 | 69.7 | 59.9 |
| 2 | Glass | 4 | 20 | TW + fabric | 0 | 68.7 | 48.0 |
| 3 | Glass | 4 | 25 | TW + fabric | 0 | 66.4 | 46.5 |
| 4 | Glass | 4 | 30 | TW + fabric | 0 | 65.5 | 46.5 |
| 5 | Glass | 4 | 35 | TW + fabric | 0 | 64.4 | 46.4 |

Determination of the Water-absorbing Capacity of the Invention-design Fabric

Figure 31:
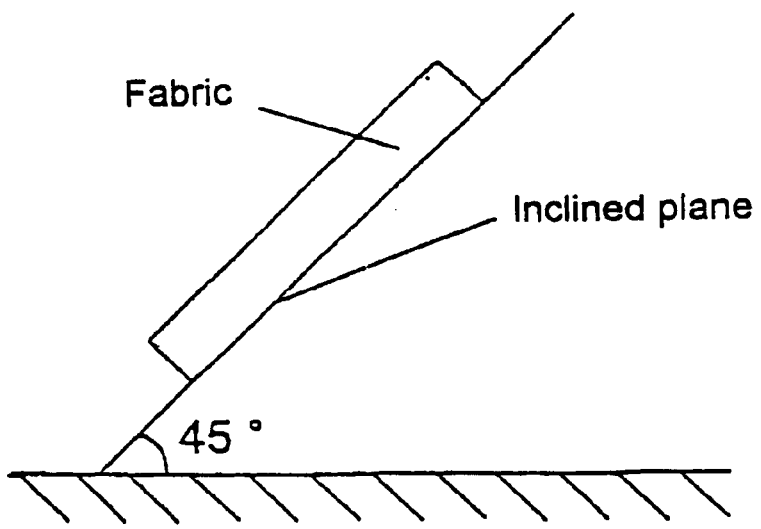
FIG. 31 shows an experimental set-up to measure the water-absorbing capacity of the invention-design fabric.

The weight-related water-absorbing capacity or retention capacity of the invention-design fabric was investigated. The water-retention capacity of the fabric was investigated on a surface inclined by 45° for 60 seconds at ambient temperature and water saturation. The arrangement as shown in FIG. 31 was employed.

Test Description

The dry fabric was first weighed and then soaked in a sufficient quantity of water for 20 minutes. The dripping-wet fabric was subsequently placed on an inclined plane (FIG. 31) for 60 seconds and then weighed again immediately. The water-absorbing capacity is derived from the difference between the weight of the waterlogged fabric and the dry weight of the fabric. This test was repeated about 8 times, whereby the fabric was returned to the water for 2 minutes between each test to absorb water. The arithmetic mean was determined from the individual values. The test was carried out at ambient temperature (approx. 22° C.).

Table 11 shows the water-retention capacity of the fabrics. The fabrics were each soaked for 20 minutes before the tests started. There was an interval of 2 minutes between each measurement.

TABLE 11

Water-retention capacity of the fabrics

| Fabric | Dry weight [g] | Drained weight [g] | Water mass [g] | Water-retention capacity (x times dry weight) |
|---|---|---|---|---|
| L01 single-sided | 16.1 | 84.04 | 67.94 | 4.22 |
| L02 single-sided | 16.69 | 110.04 | 93.35 | 5.59 |
| S10 single-sided | 15.53 | 99.72 | 84.19 | 5.42 |
| L01 double-sided | 35.87 | 188.08 | 152.21 | 4.24 |
| L02 double-sided | 38.44 | 267.81 | 229.37 | 5.97 |
| S10 double-sided | 41.31 | 207.88 | 166.57 | 4.03 |

The amount of water retained by the respective fabrics was determined from the difference between the drained and the dry weight. Table 11 shows that each fabric is capable of retaining between 4 and 6 times its dry weight in water.

Figure 32:
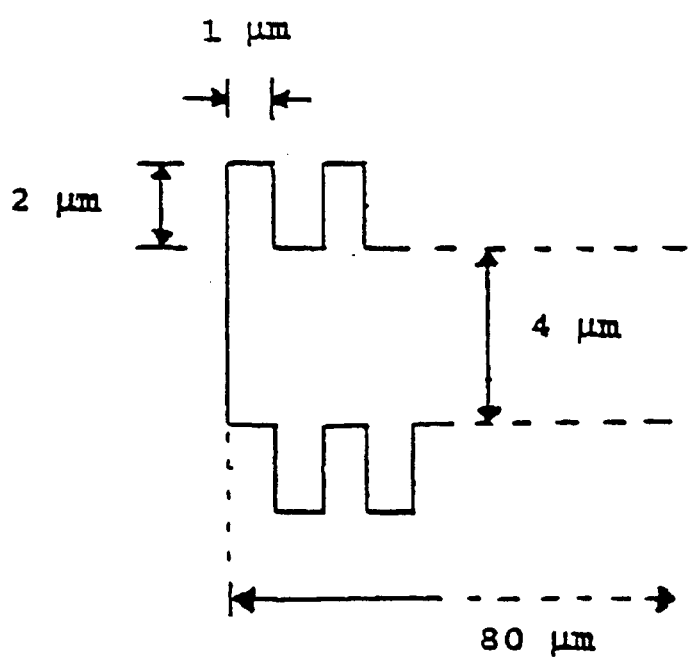
FIG. 32 shows a model to permit calculation of the specific surface area of the invention-design fabric.

Model to Permit Calculation of the Specific Surface Area of the Invention-design Fabric The following values were assumed as examples for this calculation (see FIG. 32):

| Filament width | 80 $\mu$m |
|---|---|
| Filament base structure height | 4 $\mu$m |
| Lamella height | 2 $\mu$m |
| Lamella width | 1 $\mu$m |

It therefore follows that:

1.) Cross-sectional line length of a filament 2×40×6 $\mu$m+2×4 $\mu$m=488 $\mu$m 2.) Production-specific filament length: 0.5 cm Surface area of a single filament: 488 $\mu$m×0.5 $\mu$m=244×$10^{-4}$ cm$^2$ One fibre contains 80 filaments; the average number of fibres per square millimeter is 9 fibres.

This equates to a specific surface area per square centimeter of 72000×244×$10^{-4}$ cm$^2$=1756.8 cm$^2$ surface area per square centimeter of fabric area.

A cloth made of double-sided fabric measuring 20 cm×23 cm (460 cm$^2$) therefore has a surface area of 161.62 m$^2$.

What is claimed is:

1. A process to manufacture a cellulose fibre having fibre-parallel lamellae with spacing between 1 nm and 5 $\mu$m from hydrate cellulose, the method comprising the following steps:

a) selecting shoots no older than 1 year of deciduous trees or conifers;

b) deriving wood pulp from the shoots;

c) treating the wood pulp derived from shoots no older than 1 year of deciduous tees or conifers with an alkali metal hydroxide solution to obtain an alkali cellulose;

d) pressing out superfluous alkali metal hydroxide solution from the alkali cellulose;

e) shredding the alkali cellulose into alkali cellulose crumbs;

f) ripening the alkali cellulose crumbs to a maturity of between 5° and 30° Hottenroth to form ripened crumbs;

g) treating the ripened crumbs with a wet sulphide process to form sulphadised cellulose;

h) rinsing and diluting of the sulphadised cellulose with water to obtain a spinning solution;

i) ripening of the spinning solution to a maturity of between 5° and 30° Hottenroth;

j) filtering and downstream deaerating the spinning solution;

k) injecting the spinning solution into a regenerating bath under application of spinnerets;

l) stripping the coagulating fibres off of the spinnerets with simultaneous twisting in order to obtain twisted fibres;

m) dehydrating the twisted fibres;

n) desulphurising the twisted fibres;

o) washing the twisted fibres with water;

p) predehydrating the twisted fibres; and q) drying the twisted fibres, whereby the fibres have fibre-parallel lamellae with spacing between 1 nm and 5 $\mu$m.

2. Process in accordance with claim 1, characterised in that the wood pulp derives from shoots no older than 1 year of false acacia trees, teak trees, bongassi trees or bamboo.

3. Process in accordance with claim 1, characterised in that the lignin content of the less-than-one-year-old shoots used does not exceed 7%.

4. Process in accordance with claim 1, characterized in that the alkali metal hydroxide solution used to treat the wood pulp in Step c) is a sodium hydroxide solution which contains between 150 and 350 g/l of sodium hydroxide.

5. Process in accordance with claim 4, characterised in that the sodium hydroxide solution contains approx. 300 g/l of sodium hydroxide.

6. Process in accordance with claim 1, characterized in that treatment of the wood pulp in Step c) is carried out at a temperature ranging between 15° C. and 25° C.

7. Process in accordance with claim 1, characterized in that the shredding process of the alkali cellulose in Step e) comprises a course comminution step and a fine comminution step.

8. Process in accordance with claim 1, characterized in that the alkali cellulose crumbs in Step f) are ripened at a temperature ranging between 60° C. and 75° C.

9. Process in accordance with claim 8, characterized in that the alkali cellulose crumbs are ripened at a temperature of between 65° C. and 75° C.

10. Process in accordance with claim 9, characterised in that the alkali cellulose crumbs are ripened at a temperature of approx. 72° C.

11. Process in accordance with claim 1, characterized in that the alkali cellulose crumbs in Step f) are ripened to maturity of between 8° and 12° Hottenroth.

12. Process in accordance with claim 11, characterised in that the alkali cellulose crumbs are ripened to a maturity of about 10° Hottenroth.

13. Process in accordance with claim 1, characterized in that the wet sulphide process in Step (g) is carried out in a solution containing between 150 and 250 g/l carbon disulphide and between 250 and 350 g/l sodium hydroxide.

14. Process in accordance with claim 1, characterized in that the wet sulphide process in Step (g) is carried out in solution containing between 180 and 210 g/l carbon disulphide and between 280 and 320 g/l sodium hydroxide.

15. Process in accordance with claim 1, characterized in that subsequent ripening of the cellulose in Step i) is carried out to a maturity of between 8° and 12° Hottenroth.

16. Process in accordance with claim 1, characterized in that the spinning solution downstream of the subsequent ripening of the cellulose and upstream of the filtration of the spinning solution is mixed with at least one other spinning solution produced using a process which comprises Steps a) to i) as described in claim 1.

17. Process in accordance with claim 1, characterized in that the temperature of the regenerating bath in Step k) is between 35° C. and 45°C.

18. Process in accordance with claim 17, characterised in that the temperature of the regenerating bath is approximately 40° C.

19. Process in accordance with claim 1, characterized in that the regenerating bath in Step k) contains between 70 and 160 g/l of sulphuric acid.

20. Process in accordance with claim 1, characterized in that the regenerating bath in Step k) contains between 0.3 and 4 g/l of zinc sulphate.

21. Process in accordance with claim 1, characterized in that the spinnerets in Step k) are heated to keep them at a temperature of between 55° C. and 75° C.

22. Process in accordance with claim 21, characterized in that the spinnerets are kept at a temperature of between 65° C. and 70° C.

23. Process in accordance with claim 21, characterized in that the spinnerets are kept at a temperature of approximately 67° C.

24. Process in accordance with claim 1, characterized in that the spinnerets in Step k) are oval to long-slit-shaped.

25. Process in accordance with claim 1, characterized in that dehydrating of the fibres in Step m) is carried out with a sulphuric acid solution which contains up to 15 g/l of sulphuric acid.

26. Process in accordance with claim 25, characterised in that the sulphuric acid solution used to dehydrate the fibres contains up to 10 g/l of sulphuric acid.

27. Process in accordance with claim 1, characterized in that desulphurisation of the fibres in Step n) is carried out with a sodium sulphate solution which contains between 2 and 5 g/l of sodium sulphate.

28. Process in accordance with claim 27, characterised in that the sodium sulphate solution used to desulphurise the fibres contains approximately 3 g/l of sodium sulphate.

29. Process in accordance with claim 1, characterised in that the twisted fibres are treated with titanium dioxide after being washed with water and before being dehydrated.

30. Process in accordance with claim 1, characterized in that the prehydrating of the fibres in Step p) is carried out with compressed air.

31. Process in accordance with claim 1, characterized in that the drying of the fibres in Step q) is carried out under application of tunnel dryers.

32. Process in accordance with claim 1, characterized in that the lignin content of the less-than-one-year-old shoots used does not exceed 5%.

33. Process in accordance with claim 1, characterized in that the lignin content of the less-than-one-year-old shoots used does not exceed 2%.

34. Process in accordance with claim 1, characterized in that the regenerating bath in Step k) contains between 90 and 140 g/l of sulphuric acid.

35. Process in accordance with claim 1, characterized in that the regenerating bath in Step k) contains approximately 120 g/l of sulphuric acid.

36. Process in accordance with claim 1, characterized in that the regenerating bath in Step k) contains between 0.5 and 2 g/l of zinc sulphate.

37. Process in accordance with claim 1, characterized in that the regenerating bath in Step k) contains approximately 1 g/l of zinc sulphate.

38. Cellulose fibre, produced by a process in accordance with claim 1.

39. Cellulose fibre in accordance with claim 38, characterised by a microstructure which displays fibre-parallel lamellae.

40. Cellulose fibre in accordance with claim 39, characterised in that the spacing between the fibre-parallel lamellae ranges between 1 nm and 5 μm.

41. Cellulose fibre in accordance with claim 40, characterised in that the spacing between the fibre-parallel lamellae ranges between 200 nm and 1 μm.

42. Fabric comprising:
a) a backing fabric; and
b) a pile comprising fibers in accordance with claim 38; wherein the pile is woven into the backing fabric.

43. Fabric in accordance with claim 42, characterized in that the backing fabric has a lattice structure.

44. Fabric in accordance with claim 42, characterised in that the pile forms a fibre bed of approx. 0.5 cm in height above the backing fabric.

45. Fabric in accordance with claim 42, characterised in that the backing fabric contains viscose staple fibres.

46. Fabric in accordance with claim 45, characterised in that the backing fabric consists exclusively of viscose staple fibres.

47. Fabric in accordance with claim 42, characterised in that the pile contains oval and tape fibres.

48. A cleaning and decontamination fabric made in accordance with claim 42.

49. A water surface tension reducer comprising a fabric in accordance with claim 42.

50. A textile comprising a fabric in accordance with claim 42.

51. A clothing textile comprising a fabric in accordance with claim 42.

52. A personal hygiene article comprising a fabric in accordance with claim 42.

53. A particle filter comprising a fabric in accordance with claim 42.

54. A condensation catalyst comprising a fabric in accordance with claim 42.

55. A floor covering comprising a fabric in accordance with claim 42.

56. A covering material comprising a fabric in accordance with claim 42.

57. Fabric comprising a backing fabric and a pile woven into the backing fabric, wherein the pile is comprised of cellulose fibers formed by:
  a) treating wood pulp derived from shoots no older than 1 year of deciduous trees or conifers with an alkali metal hydroxide solution in order to obtain an alkali cellulose;
  b) pressing out the superfluous alkali metal hydroxide solution from the obtained alkali cellulose;
  c) shredding the alkali cellulose into crumbs;
  d) ripening the alkali cellulose crumbs to a maturity of between 5° and 30° Hottenroth;
  e) employing a wet sulfide process to treat the ripened crumbs in order to sulfadize the cellulose;
  f) rinsing and diluting the sulfadized cellulose with water in order to obtain a spinning solution;
  g) subsequenty ripening the rinsed and diluted cellulose to a maturity of between 5° and 30° Hottenroth;
  h) filtering and deaerating the spinning solution;
  i) injecting the spinning solution into a regenerating bath under application of spinnerets;
  j) stripping off the coagulating fibers with simultaneous twisting in order to obtain twisted fibers;
  k) dehydrating the twisted fibers;
  l) desulfurizing the twisted fibers;
  m) washing the twisted fibers with water;
  n) predehydrating the twisted fibers; and
  o) drying the twisted fibers;
the fabric characterised in that the pile consists of 50% oval fibers and 50% tape fibers.

58. Fabric comprising a backing fabric and a pile woven into the backing fabric, wherein the pile is comprised of cellulose fibers formed by:
  a) treating wood pulp derived from shoots no older than 1 year of deciduous trees or conifers with an alkali metal hydroxide solution in order to obtain an alkali cellulose;
  b) pressing out the superfluous alkali metal hydroxide solution from the obtained alkali cellulose;
  c) shredding the alkali cellulose into crumbs;
  d) ripening the alkali cellulose crumbs to a maturity of between 5° and 30° Hottenroth;
  e) employing a wet sulfide process to treat the ripened crumbs in order to sulfadize the cellulose;
  f) rinsing and diluting the sulfadized cellulose with water in order to obtain a spinning solution;
  g) subsequently ripening the rinsed and diluted cellulose to a maturity of between 5° and 30° Hottenroth;
  h) filtering and deaerating the spinning solution;
  i) injecting the spinning solution into a regenerating bath under application of spinnerets;
  j) stripping off the coagulating fibers with simultaneous twisting in order to obtain twisted fibers;
  k) dehydrating the twisted fibers;
  l) desulfurizing the twisted fibers;
  m) washing the twisted fibers with water;
  n) predehydrating the twisted fibers; and
  o) drying the twisted fibers;
the fabric characterized in that the pile consists of 50% of oval fibers with a count of 330 dtex F60 and 50% of tape fibers with a count of 300 dtex F80.

* * * * *